United States Patent
Nelson Konen et al.

(10) Patent No.: US 9,687,603 B2
(45) Date of Patent: Jun. 27, 2017

(54) VOLUME MONITORING FOR IMPLANTABLE FLUID DELIVERY DEVICES

(75) Inventors: Cynthia R. Nelson Konen, Anoka, MN (US); Irfan Z. Ali, Woodbury, MN (US); Keith A. Miesel, St. Paul, MN (US); Scott L. Kalpin, Harris, MN (US)

(73) Assignee: Medtronic, Inc., Minneapolis, MN (US)

( * ) Notice: Subject to any disclaimer, the term of this patent is extended or adjusted under 35 U.S.C. 154(b) by 660 days.

(21) Appl. No.: 12/762,064

(22) Filed: Apr. 16, 2010

(65) Prior Publication Data

US 2011/0257591 A1 Oct. 20, 2011

(51) Int. Cl.
*A61M 5/142* (2006.01)
*A61M 5/168* (2006.01)

(52) U.S. Cl.
CPC ...... *A61M 5/1684* (2013.01); *A61M 5/14276* (2013.01); *A61M 5/16854* (2013.01); *A61M 2005/14264* (2013.01); *A61M 2205/3331* (2013.01); *A61M 2205/3379* (2013.01); *A61M 2205/3389* (2013.01)

(58) Field of Classification Search
CPC .......... A61M 5/14276; A61M 5/16854; A61M 5/1685; A61M 2005/14264; A61M 5/172; A61M 2205/3379; A61M 2205/3389; A61M 2205/3331
USPC ............... 604/67, 65, 505; 702/55; 700/281; 340/540
See application file for complete search history.

(56) References Cited

U.S. PATENT DOCUMENTS

| | | | | |
|---|---|---|---|---|
| 4,373,527 A | * | 2/1983 | Fischell | A61M 5/14276 128/903 |
| 4,395,259 A | | 7/1983 | Prestele et al. | |
| 4,443,218 A | | 4/1984 | Decant, Jr. et al. | |
| 4,486,190 A | * | 12/1984 | Reinicke | A61M 5/14276 604/67 |
| 4,561,298 A | * | 12/1985 | Pond | G01F 17/00 73/149 |
| 4,718,430 A | | 1/1988 | Holzer | |

(Continued)

FOREIGN PATENT DOCUMENTS

| | | |
|---|---|---|
| EP | 0622615 A1 | 11/1994 |
| EP | 1649884 A1 | 4/2006 |

(Continued)

OTHER PUBLICATIONS

U.S. Appl. No. 12/762,108, filed Apr. 16, 2010, Kalpin.

(Continued)

*Primary Examiner* — Bhisma Mehta
*Assistant Examiner* — Jenna Zhang
(74) *Attorney, Agent, or Firm* — Shumaker & Sieffert, P.A.

(57) ABSTRACT

Unexpected changes in the volume of therapeutic fluid in the reservoir of a fluid delivery device are detected based on changes in the pressure of the reservoir measured over a period of time by a pressure sensor. Additionally, an ambulatory reservoir fluid volume gauge is provided to indicate an actual volume of therapeutic fluid in a fluid delivery device reservoir. The actual volume of therapeutic fluid in the reservoir indicated by the ambulatory reservoir fluid volume gauge is determined based on changes in the pressure in the reservoir measured over a period of time by a pressure sensor.

60 Claims, 7 Drawing Sheets

(56) References Cited

U.S. PATENT DOCUMENTS

| | | | |
|---|---|---|---|
| 4,784,645 A | 11/1988 | Fischell | |
| 4,840,064 A | 6/1989 | Fudim | |
| 4,881,185 A | 11/1989 | Murakami et al. | |
| 5,006,997 A | 4/1991 | Reich | |
| 5,132,923 A | 7/1992 | Crawford et al. | |
| 5,319,964 A | 6/1994 | Stephensen et al. | |
| 5,472,420 A | 12/1995 | Campbell | |
| 5,507,737 A * | 4/1996 | Palmskog | A61M 5/14276 128/903 |
| 5,904,666 A | 5/1999 | DeDecker et al. | |
| 6,022,483 A * | 2/2000 | Aral | B01J 3/006 156/345.26 |
| 6,163,979 A | 12/2000 | Oetjen et al. | |
| 6,280,408 B1 * | 8/2001 | Sipin | A61M 5/1483 604/65 |
| 6,302,864 B1 | 10/2001 | Nowosielski | |
| 6,315,769 B1 | 11/2001 | Peer et al. | |
| 6,321,597 B1 * | 11/2001 | Demers | G01F 22/02 73/149 |
| 6,542,848 B1 * | 4/2003 | Neeser | F17C 13/025 700/281 |
| 6,562,001 B2 | 5/2003 | Lebel et al. | |
| 6,740,059 B2 | 5/2004 | Flaherty | |
| 6,810,308 B2 * | 10/2004 | Shajii | G01F 1/684 137/599.05 |
| 6,882,960 B2 * | 4/2005 | Miller | F04B 51/00 702/177 |
| 6,939,111 B2 * | 9/2005 | Huitt | A61M 1/28 417/42 |
| 7,054,782 B2 | 5/2006 | Hartlaub | |
| 7,137,964 B2 | 11/2006 | Flaherty | |
| 7,206,715 B2 | 4/2007 | Vanderveen et al. | |
| 7,694,591 B2 | 4/2010 | Leibfried | |
| 7,890,273 B2 | 2/2011 | Lovell et al. | |
| 8,313,308 B2 | 11/2012 | Lawless et al. | |
| 2002/0087116 A1 | 7/2002 | Hartlaub | |
| 2002/0161328 A1 | 10/2002 | Rogers | |
| 2003/0084589 A1 | 5/2003 | Chowdhury et al. | |
| 2004/0249336 A1 | 12/2004 | Faries et al. | |
| 2004/0260233 A1 | 12/2004 | Garibotto et al. | |
| 2005/0010164 A1 * | 1/2005 | Mantell | A61M 13/003 604/26 |
| 2005/0033197 A1 | 2/2005 | Cottler | |
| 2005/0075624 A1 | 4/2005 | Miesel | |
| 2005/0187515 A1 | 8/2005 | Varrichio et al. | |
| 2005/0214129 A1 | 9/2005 | Greene et al. | |
| 2006/0089619 A1 | 4/2006 | Ginggen | |
| 2006/0149220 A1 | 7/2006 | Ullestad et al. | |
| 2006/0206054 A1 * | 9/2006 | Shekalim | A61M 5/1454 604/122 |
| 2006/0219017 A1 | 10/2006 | Silverbrook et al. | |
| 2006/0276744 A1 | 12/2006 | Falk | |
| 2007/0068528 A1 * | 3/2007 | Bohm | A61B 5/085 128/204.23 |
| 2007/0088267 A1 * | 4/2007 | Shekalim | A61M 5/145 604/134 |
| 2007/0106280 A1 | 5/2007 | Utard et al. | |
| 2007/0225924 A1 | 9/2007 | Hashizume et al. | |
| 2007/0239381 A1 | 10/2007 | Ginggen et al. | |
| 2007/0250005 A1 * | 10/2007 | Fago | A61M 5/31525 604/113 |
| 2007/0250045 A1 | 10/2007 | Trieu | |
| 2007/0255259 A1 | 11/2007 | Miesel | |
| 2007/0264130 A1 * | 11/2007 | Mallett | A61M 5/14526 417/38 |
| 2008/0125702 A1 | 5/2008 | Blischak et al. | |
| 2008/0243093 A1 | 10/2008 | Kalpin et al. | |
| 2009/0082757 A1 | 3/2009 | Rogers et al. | |
| 2009/0221986 A1 * | 9/2009 | Wang | A61M 5/16877 604/503 |
| 2009/0270844 A1 | 10/2009 | Seeley et al. | |
| 2010/0125246 A1 | 5/2010 | Kalpin | |
| 2010/0137842 A1 | 6/2010 | Gibson | |
| 2010/0274180 A1 * | 10/2010 | Donovan | A61B 17/8872 604/65 |
| 2010/0288788 A1 | 11/2010 | Ophardt | |
| 2011/0166544 A1 * | 7/2011 | Verhoef | A61M 5/1413 604/500 |

FOREIGN PATENT DOCUMENTS

| | | |
|---|---|---|
| EP | 1839635 A1 | 10/2007 |
| WO | 0072900 A1 | 12/2000 |
| WO | 0228454 A2 | 4/2002 |
| WO | 03068049 A2 | 8/2003 |
| WO | 2007041471 A2 | 4/2007 |
| WO | 2008121421 A1 | 10/2008 |
| WO | 2009137780 A2 | 11/2009 |
| WO | 2010/059588 A1 | 5/2010 |

OTHER PUBLICATIONS

U.S. Appl. No. 12/762,121, filed Apr. 16, 2010, Kalpin.

Notification of Transmittal of the International Search Report and the Written Opinion of the International Searching Authority for corresponding patent application No. PCT/US2011/023086, mailed Oct. 12, 2011, 16 pages.

Office action from U.S. Appl. No. 12/762,108, dated Aug. 6, 2013, 31 pp.

Office action from U.S. Appl. No. 12/762,121, dated Aug. 6, 2013, 21 pp.

Watsham et al., excerpt from Quantitative Methods in Finance, 1997, p. 103.

Response to office action for U.S. Appl. No. 12/762,108, filed Apr. 8, 2013, 18 pages.

Office action for U.S. Appl. No. 12/762,108, mailed Jan. 7, 2013, 27 pages.

Notice of Allowance from U.S. Appl. No. 12/762,108, dated Apr. 11, 2014, 13 pp.

Office Action from U.S. Appl. No. 12/762,121 dated Mar. 7, 2014, 22 pp.

Response to Office Action dated Aug. 6, 2013, from U.S. Appl. No. 12/762,121, filed Nov. 6, 2013, 6 pp.

Response to Office Action dated Aug. 6, 2013, from U.S. Appl. No. 12/762,108, filed Nov. 6, 2013, 21 pp.

* cited by examiner

VOLUME MONITORING FOR IMPLANTABLE FLUID DELIVERY DEVICES

TECHNICAL FIELD

This disclosure relates generally to implantable medical devices and, more particularly, to implantable fluid delivery devices.

BACKGROUND

A variety of medical devices are used for chronic, i.e., long-term, delivery of fluid therapy to patients suffering from a variety of conditions, such as chronic pain, tremor, Parkinson's disease, epilepsy, urinary or fecal incontinence, sexual dysfunction, obesity, spasticity, or gastroparesis. For example, pumps or other fluid delivery devices can be used for chronic delivery of therapeutic fluids, such as drugs to patients. These devices are intended to provide a patient with a therapeutic output to alleviate or assist with a variety of conditions. Typically, such devices are implanted in a patient and provide a therapeutic output under specified conditions on a recurring basis.

One type of implantable fluid delivery device is a drug infusion device that can deliver a drug or other therapeutic fluid to a patient at a selected site. A drug infusion device may be partially or completely implanted at a location in the body of a patient and deliver a fluid medication through a catheter to a selected delivery site in the body. Drug infusion devices, such as implantable drug pumps, commonly include a reservoir for holding a supply of the therapeutic fluid, such as a drug, for delivery to a site in the patient. The fluid reservoir can be self-sealing and accessible through one or more ports. A pump is fluidly coupled to the reservoir for delivering the therapeutic fluid to the patient. A catheter provides a pathway for delivering the therapeutic fluid from the pump to a delivery site in the patient.

SUMMARY

In general, this disclosure describes techniques for detecting unexpected changes in a volume of therapeutic fluid in a reservoir of an implantable fluid delivery device and for controlling an ambulatory reservoir fluid volume gauge to indicate an actual volume of fluid in the reservoir based on changes in a pressure of the reservoir over a period of time. The pressure of the reservoir may be measured by a pressure sensor. The volume of the fluid in the reservoir may undergo an expected change as the fluid is delivered to a patient, e.g., according to a therapy program, which may be tracked and indicated to users by an ambulatory reservoir fluid volume gauge. In some cases, detection of an unexpected change in volume may indicate unintended leakage of fluid, unauthorized fluid removal or other anomalies.

In one example, an implantable therapeutic fluid delivery system includes a reservoir configured to house a therapeutic fluid. A pressure sensor is configured to measure a pressure of the reservoir. A processor is configured to detect an unexpected change in a volume of the therapeutic fluid in the reservoir based on changes in the pressure of the reservoir measured by the pressure sensor over time.

In another example, a method includes measuring a pressure of a reservoir of a fluid delivery device with a pressure sensor and detecting an unexpected change in a volume of therapeutic fluid in the reservoir based on changes in the pressure of the reservoir measured by the pressure sensor over time.

In another example, a computer-readable storage medium contains instructions for causing a programmable processor to cause a pressure sensor to measure a pressure of a reservoir of a fluid delivery device with a pressure sensor and detect an unexpected change in a volume of therapeutic fluid in the reservoir based on changes in the pressure of the reservoir measured by the pressure sensor over time.

In another example, a fluid delivery system includes means for measuring a pressure of a reservoir of a fluid delivery device with a pressure sensor and means for detecting an unexpected change in a volume of therapeutic fluid in the reservoir based on changes in the pressure of the reservoir measured by the means for measuring the pressure of the reservoir over time.

In another example, a therapeutic fluid delivery system includes a reservoir is configured to house a therapeutic fluid. A pressure sensor is configured to measure a pressure of the reservoir. A processor is configured to determine an actual volume of the therapeutic fluid in the reservoir based on changes in the pressure of the reservoir measured by the pressure sensor over time and to control an ambulatory fluid volume gauge to indicate the actual volume of the therapeutic fluid in the reservoir.

In another example, a method includes measuring a pressure of a reservoir of a fluid delivery device with a pressure sensor, determining an actual volume of therapeutic fluid in the reservoir based on changes in the pressure of the reservoir measured by the pressure sensor over time, and controlling an ambulatory fluid volume gauge to indicate the actual volume of therapeutic fluid in the reservoir.

In another example, a fluid delivery system includes means for measuring a pressure of a reservoir of a fluid delivery device with a pressure sensor, means for determining an actual volume of therapeutic fluid in the reservoir based on changes in the pressure of the reservoir measured by the pressure sensor over time, and means for controlling an ambulatory fluid volume gauge to indicate the actual volume of therapeutic fluid in the reservoir.

In another example, a method includes measuring a pressure of a reservoir of a fluid delivery device with a pressure sensor, determining an actual rate at which the therapeutic fluid is delivered from the reservoir based on changes in the pressure of the reservoir measured by the pressure sensor, integrating the actual rate at which the therapeutic fluid is delivered from the reservoir over a period of time over which changes in the pressure of the reservoir are measured by the pressure sensor to determine an actual volume of therapeutic fluid in the reservoir, and controlling an ambulatory fluid volume gauge to indicate the actual volume of therapeutic fluid in the reservoir.

In another example, a computer-readable storage medium comprising instructions for causing a programmable processor to measure a pressure of a reservoir of a fluid delivery device with a pressure sensor, determine an actual volume of therapeutic fluid in the reservoir based on changes in the pressure of the reservoir measured by the pressure sensor over time, and control an ambulatory fluid volume gauge to indicate the actual volume of therapeutic fluid in the reservoir.

The details of one or more examples disclosed herein are set forth in the accompanying drawings and the description below. Other features, objects, and advantages will be apparent from the description and drawings, and from the claims.

DETAILED DESCRIPTION

Figure 1:
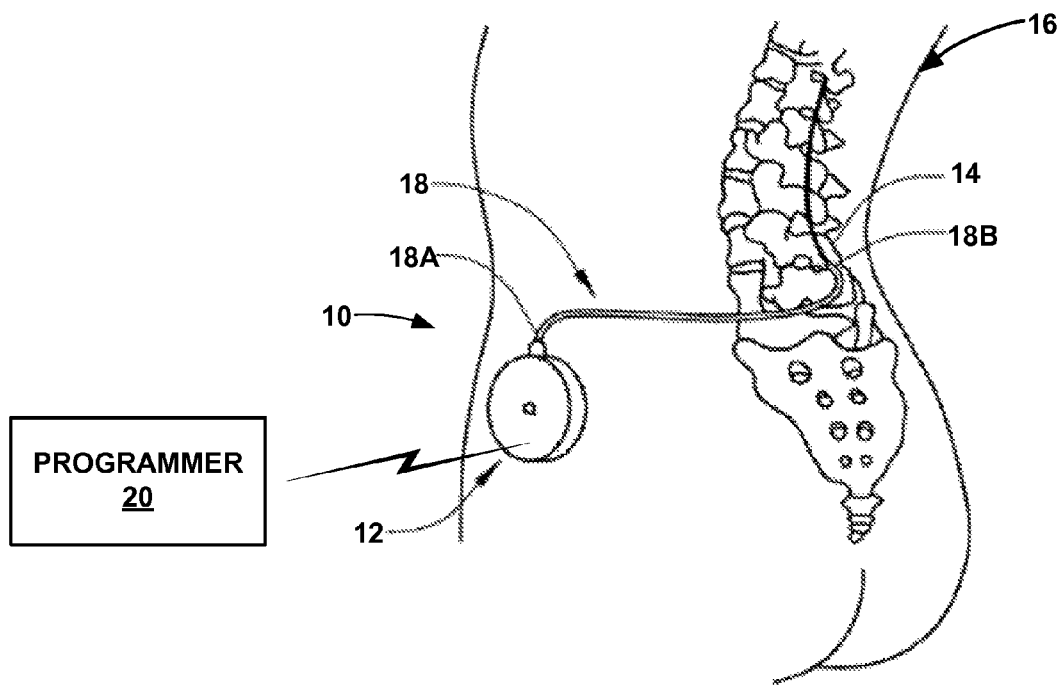
FIG. 1 is a conceptual diagram illustrating an example of a fluid delivery system including an implantable fluid delivery device configured to deliver a therapeutic fluid to a patient via a catheter.

This application is related to U.S. patent application Ser. No. 12/619,145, filed Nov. 16, 2009, which claims the benefit of U.S. Provisional Application Ser. No. 61/116,309, filed Nov. 20, 2008, both of which applications are incorporated herein by this reference. This application is also related to U.S. patent application Ser. No. 12/199,536, filed Aug. 27, 2008, which claims the benefit of U.S. Provisional Application Ser. No. 60/975,286, filed Sep. 26, 2007, both of which applications are incorporated herein by this reference.

It is generally useful for the safe and intended operation of fluid delivery devices to monitor the volume of therapeutic fluid in the reservoir of the device as the fluid is being delivered to a patient. For example, it may be generally useful to monitor the fluid in the reservoir to detect unexpected changes in the volume of fluid in the device.

An unexpected change in fluid volume may occur when the patient or another person, outside of a clinical environment, attempts to access the refill port of the reservoir to remove therapeutic fluid from the device. Another cause of unexpected changes in fluid volume in the reservoir may be valve leakage or pump stroke volume variation. Although the pump of a given fluid delivery device may be designed with a constant stroke volume, material build up in the pump mechanism can change the physical configuration of the pump such that stroke volume also changes.

Unexpected changes in reservoir volume may affect the intended operation of the device by underdosing or overdosing of the patient with the therapeutic fluid delivered by the fluid delivery device. Underdosing of the patient may be of particular interest in cases where rapidly reducing the amount of therapeutic fluid delivered by the device to the patient may cause withdrawal symptoms.

Device awareness of reservoir fluid volume may be important for the foregoing and other reasons related to the proper operation of fluid delivery devices and the efficacious delivery of therapy to patients by such devices. For example, in addition to detecting unexpected therapeutic fluid volume changes, is also useful to monitor the volume of therapeutic fluid in the reservoir of an implantable medical device (IMD) as the fluid is being delivered to a patient to provide an ambulatory reservoir volume gauge. Fluid delivery devices commonly track and may, in some cases, report reservoir volume to users. However, the reservoir volume is based not on an actual measured volume of fluid in the reserve, but on the expected volume of fluid in the reservoir based on a known starting volume and a programmed therapeutic fluid dispense rate. Because various operational factors may cause the expected volume calculation to become less accurate over time, it may be advantageous to supplement or replace the expected volume calculation with an actual measured volume to provide a more accurate ambulatory reservoir volume gauge to users.

The term ambulatory volume gauge is used in this disclosure to refer to tracking and reporting the volume of therapeutic fluid in a fluid delivery device reservoir during the normal operation of the device to deliver the fluid to a patient. This is in contrast to, for example, monitoring the volume of fluid in the reservoir during a therapeutic fluid refill operation.

In view of the advantages of monitoring reservoir fluid volume for fluid delivery devices, or other similar devices, techniques are disclosed in which unexpected changes in the volume of therapeutic fluid in the reservoir are detected based on changes in the pressure of the reservoir measured over a period of time by a pressure sensor. Additionally, techniques are disclosed in which an ambulatory reservoir volume gauge is based on an actual volume of therapeutic fluid in the reservoir determined based on changes in the pressure in the reservoir measured over a period of time by a pressure sensor. Particular techniques for detecting unexpected changes in reservoir fluid volume and providing an ambulatory reservoir volume gauge will be described in greater detail with reference to FIGS. 4 and 5. However, an example fluid delivery system including an implantable fluid delivery device and external programmer will first be described with reference to FIGS. 1-3.

FIG. 1 is a conceptual diagram illustrating an example of a therapy system 10, which includes IMD 12, catheter 18, and external programmer 20. IMD 12 is connected to catheter 18 to deliver at least one therapeutic fluid, e.g. a pharmaceutical agent, pain relieving agent, anti-inflammatory agent, gene therapy agent, or the like, to a target site within patient 16. IMD 12 includes an outer housing that, in some examples, is constructed of a biocompatible material that resists corrosion and degradation from bodily fluids including, e.g., titanium or biologically inert polymers. IMD 12 may be implanted within a subcutaneous pocket relatively close to the therapy delivery site. For example, in the example shown in FIG. 1, IMD 12 is implanted within an abdomen of patient 16. In other examples, IMD 12 may be implanted within other suitable sites within patient 16, which may depend, for example, on the target site within patient 16 for the delivery of the therapeutic fluid. In still other examples, IMD 12 may be external to patient 16 with a percutaneous catheter connected between IMD 12 and the target delivery site within patient 16.

IMD 12 delivers a therapeutic fluid from a reservoir (not shown) to patient 16 through catheter 18 from proximal end 18A coupled to IMD 12 to distal end 18B located proximate to the target site. Example therapeutic fluids that may be delivered by IMD 12 include, e.g., insulin, morphine, hydromorphone, bupivacaine, clonidine, other analgesics, baclofen and other muscle relaxers and antispastic agents, genetic agents, antibiotics, nutritional fluids, hormones or hormonal drugs, gene therapy drugs, anticoagulants, cardiovascular medications or chemotherapeutics.

Catheter 18 can comprise a unitary catheter or a plurality of catheter segments connected together to form an overall catheter length. External programmer 20 is configured to wirelessly communicate with IMD 12 as needed, such as to provide or retrieve therapy information or control aspects of therapy delivery (e.g., modify the therapy parameters such as rate or timing of delivery, turn IMD 12 on or off, and so forth) from IMD 12 to patient 16.

Catheter 18 may be coupled to IMD 12 either directly or with the aid of a catheter extension (not shown in FIG. 1). In the example shown in FIG. 1, catheter 18 traverses from the implant site of IMD 12 to one or more targets proximate to spinal cord 14. Catheter 18 is positioned such that one or more fluid delivery outlets (not shown in FIG. 1) of catheter 18 are proximate to the targets within patient 16. In the example of FIG. 1, IMD 12 delivers a therapeutic fluid through catheter 18 to targets proximate to spinal cord 14.

IMD 12 can be configured for intrathecal drug delivery into the intrathecal space, as well as epidural delivery into the epidural space, both of which surround spinal cord 14. In some examples, multiple catheters may be coupled to IMD 12 to target the same or different nerve or other tissue sites within patient 16, or catheter 18 may include multiple lumens to deliver multiple therapeutic fluids to the patient. Therefore, although the target site shown in FIG. 1 is proximate to spinal cord 14 of patient 16, other applications of therapy system 10 include alternative target delivery sites in addition to or in lieu of the spinal cord of the patient.

Programmer 20 is an external computing device that is configured to communicate with IMD 12 by wireless telemetry. For example, programmer 20 may be a clinician programmer that the clinician uses to communicate with IMD 12 and program therapy delivered by the IMD. Alternatively, programmer 20 may be a patient programmer that allows patient 16 to view and modify therapy parameters associated with therapy programs. The clinician programmer may include additional or alternative programming features than the patient programmer. For example, more complex or sensitive tasks may only be allowed by the clinician programmer to prevent patient 16 from making undesired or unsafe changes to the operation of IMD 12. Programmer 20 may be a handheld or other dedicated computing device, or a larger workstation or a separate application within another multi-function device.

As described in greater detail below with reference to FIGS. 4 and 5, IMD 12, alone or in cooperation with programmer 20 or another external device communicatively connected to IMD 12, is configured to detect unexpected changes in the volume of therapeutic fluid in a reservoir of the device based on changes in the pressure of the reservoir measured over a period of time by a pressure sensor. In one example, IMD 12 detects unexpected changes in the volume of therapeutic fluid in the reservoir by determining a difference between an actual rate at which the therapeutic fluid is delivered from the reservoir and a rate at which the therapeutic fluid is expected to be delivered from the reservoir. In another example, IMD 12 detects unexpected changes in the volume of therapeutic fluid in the reservoir by determining a difference between an actual volume of therapeutic fluid in the reservoir, which is a function of the actual rate of fluid delivery, and an expected volume of therapeutic fluid in the reservoir.

Additionally, IMD 12, alone or in cooperation with programmer 20 or another external device communicatively connected to IMD 12, is configured to determine a volume of therapeutic fluid in the reservoir of the device based on changes in the pressure of the reservoir measured by a pressure sensor over time. IMD 12 also controls an ambulatory fluid volume gauge to indicate the determined volume of fluid in the reservoir. In one example, the ambulatory fluid volume gauge may be a display of programmer 20, which displays a text or graphical representation of the volume of fluid in the reservoir. In another example, the ambulatory fluid volume gauge may be a separate display or display of another device, e.g. a laptop, desktop, or server computer, which is communicatively connected to IMD 12 and configured to display a text or graphical representation of the volume of fluid in the reservoir.

Figure 2:
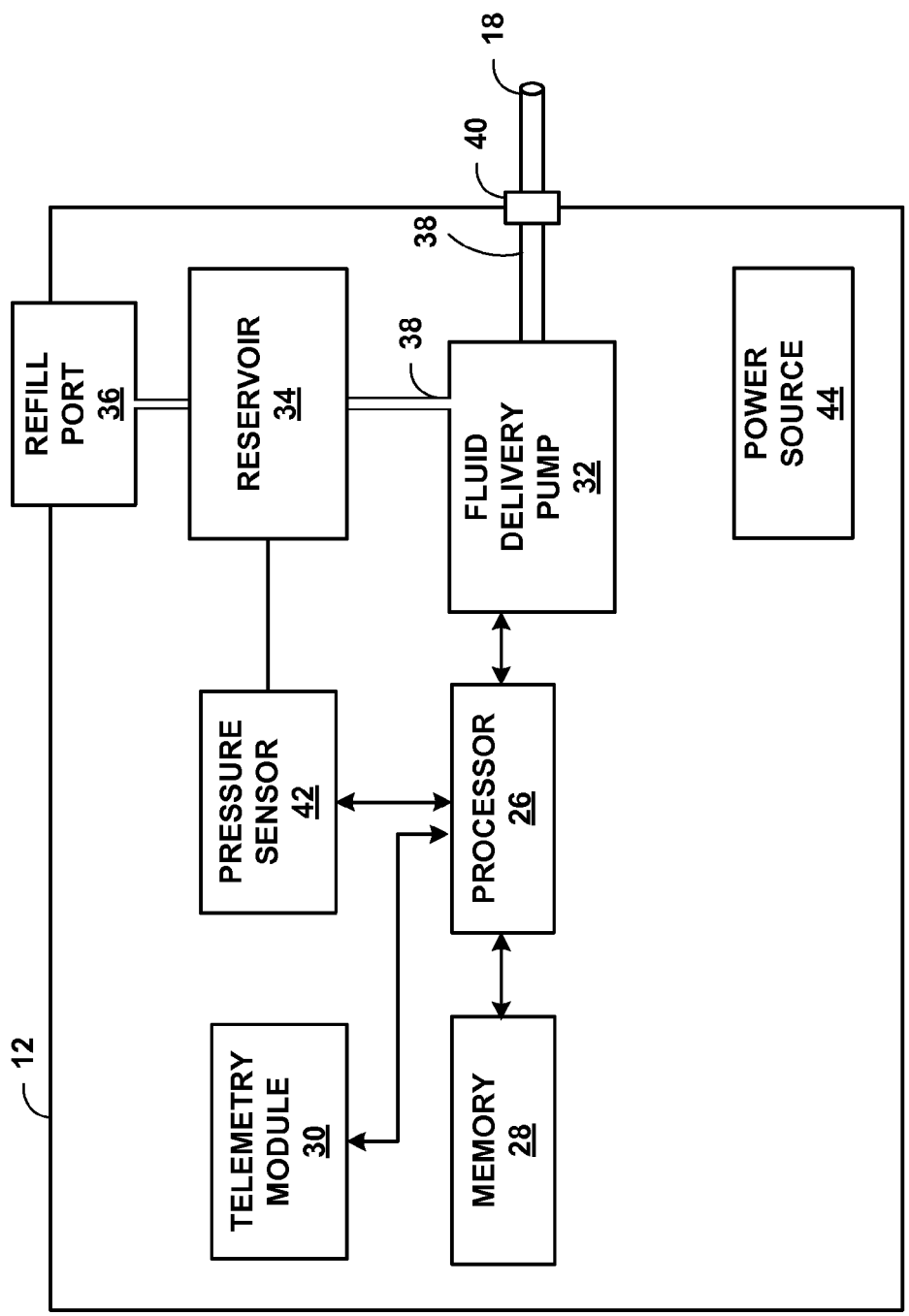
FIG. 2 is functional block diagram illustrating an example of the implantable fluid delivery device of FIG. 1.

FIG. 2 is a functional block diagram illustrating components of an example of IMD 12, which includes processor 26, memory 28, telemetry module 30, fluid delivery pump 32, reservoir 34, refill port 36, internal tubing 38, catheter access port 40, pressure sensor 42 and power source 44. Processor 26 is communicatively connected to memory 28, telemetry module 30, and fluid delivery pump 32. Fluid delivery pump 32 is connected to reservoir 34 and internal tubing 38. Reservoir 34 is connected to refill port 36. Catheter access port 40 is connected to internal tubing 38 and catheter 18.

IMD 12 also includes power source 44, which is configured to deliver operating power to various components of the IMD. In some examples, IMD 12 may include a plurality of reservoirs for storing more than one type of therapeutic fluid. In some examples, IMD 12 may include a single long tube that contains the therapeutic fluid in place of a reservoir. However, for ease of description, an IMD 12 including a single reservoir 34 is primarily described with reference to the disclosed examples.

During operation of IMD 12, processor 26 controls fluid delivery pump 32 with the aid of instructions associated with program information that is stored in memory 28 to deliver a therapeutic fluid to patient 16 via catheter 18. Instructions executed by processor 26 may, for example, define therapy programs that specify the dose of therapeutic fluid that is delivered to a target tissue site within patient 16 from reservoir 30 via catheter 18. The programs may further specify a schedule of different therapeutic fluid rates and/or other parameters by which IMD 12 delivers therapy to patient 16.

In general, a therapy program stored on memory 28 and executed by processor 26 defines one or more therapeutic fluid doses to be delivered from reservoir 34 to patient 16 through catheter 18 by IMD 12. A dose of therapeutic fluid generally refers to a total amount of therapeutic fluid, e.g., measured in milligrams or other volumetric units, delivered over a total amount of time, e.g., per day or twenty-four hour period. The amount of therapeutic fluid in a dose may convey to a caregiver an indication of the probable efficacy of the fluid and the possibility of side effects.

In general, a sufficient amount of the fluid should be administered in order to have a desired therapeutic effect, such as pain relief However, the amount of the therapeutic fluid delivered to the patient should be limited to a maximum amount, such as a maximum daily amount, in order not to avoid potential side effects. Therapy program parameters specified by a user, e.g., via programmer 20 may include fluid volume per dose, dose time period, maximum dose for a given time interval e.g., daily. In some examples, dosage may also prescribe particular concentrations of active ingredients in the therapeutic fluid delivered by IMD 12 to patient 16.

The manner in which a dose of therapeutic fluid is delivered to patient 16 by IMD 12 may also be defined in the therapy program. For example, processor 26 of IMD 12 may be programmed to deliver a dose of therapeutic fluid according to a schedule that defines different rates at which the fluid is to be delivered at different times during the dose period, e.g. a twenty-four hour period. The therapeutic fluid rate refers to the amount, e.g. in volume, of therapeutic fluid delivered over a unit period of time, which may change over the course of the day as IMD 12 delivers the dose of fluid to patient 16.

As an example, IMD 12 could be programmed to deliver therapeutic fluid to patient 16 at a rate of 20 microliters per hour. In the event the therapy program prescribes this fluid delivery rate for a twenty four hour period and assuming no patient or other boluses during the period of time, the dose of fluid delivered to patient 16 by IMD 12 will be 480 microliters (per twenty four hours). The therapy program may include other parameters, including, e.g., definitions of priming and patient boluses, as well as time intervals between successive patient boluses, sometimes referred to as lock-out intervals.

Therapy programs may be a part of a program group, where the group includes a number of therapy programs. Memory 28 of IMD 12 may store one or more therapy programs, as well as instructions defining the extent to which patient 16 may adjust therapy parameters, switch between therapy programs, or undertake other therapy adjustments. Patient 16 or a clinician may select and/or generate additional therapy programs for use by IMD 12, e.g., via external programmer 20 at any time during therapy or as designated by the clinician.

Components described as processors within IMD 12, external programmer 20, or any other device described in this disclosure may each include one or more processors, such as one or more microprocessors, digital signal processors (DSPs), application specific integrated circuits (ASICs), field programmable gate arrays (FPGAs), programmable logic circuitry, or the like, either alone or in any suitable combination.

In one example, processor 26 of IMD 12 is programmed to deliver a dose of therapeutic fluid to patient 16, which is defined in memory 28 of the device by a volume of therapeutic fluid delivered to the patient in one day. IMD 12 is also programmed according to a therapy schedule such that the fluid is delivered at different rates at different times during the day, which may be stored in the device memory, e.g., as a look-up table associating different fluid rates at different times during the day.

Upon instruction from processor 26, fluid delivery pump 32 draws fluid from reservoir 34 and pumps the fluid through internal tubing 38 to catheter 18 through which the fluid is delivered to patient 16 to effect one or more of the treatments described above in accordance with the program stored on memory 28. Internal tubing 38 is a segment of tubing or a series of cavities within IMD 12 that run from reservoir 34, around or through fluid delivery pump 32 to catheter access port 40.

Fluid delivery pump 32 can be any mechanism that delivers a therapeutic fluid in some metered or other desired flow dosage to the therapy site within patient 16 from reservoir 30 via implanted catheter 18. In one example, fluid delivery pump 32 is a squeeze pump that squeezes internal tubing 38 in a controlled manner, e.g., such as a peristaltic pump, to progressively move fluid from reservoir 34 to the distal end of catheter 18 and then into patient 16 according to parameters specified by the therapy program stored on memory 28 and executed by processor 26.

In various examples, fluid delivery pump 32 may be an axial pump, a centrifugal pump, a pusher plate pump, a piston-driven pump, or other means for moving fluid through internal tubing 38 and catheter 18. In one example, fluid delivery pump 32 is an electromechanical pump that delivers fluid by the application of pressure generated by a piston that moves in the presence of a varying magnetic field and that is configured to draw fluid from reservoir 34 and pump the fluid through internal tubing 38 and catheter 18 to patient 16.

IMD 12 includes pressure sensor 42, which is configured to measure pressure in reservoir 34. Pressure sensor 42 may be arranged in a number of locations within IMD 12 including, e.g., in reservoir 34 or refill port 26. Regardless of where arranged, pressure sensor 42 is communicatively connected to processor 26 to transmit pressure-related information to the processor for analysis and storage on memory 28 in order to, e.g., determine the actual rate at which therapeutic fluid is delivered from reservoir 34 to patient 16, and/or the actual volume of therapeutic fluid remaining in the reservoir.

Pressure sensor 42 may be electronically coupled to processor 26, or a processor of another device, in a variety of ways including electrical wiring (not shown) or a wireless link between the pressure sensor and the processing device. Pressure sensor 42 may be any device capable of measuring pressure of reservoir 34. For example, pressure sensor 42 may be a capacitive measurement device which determines pressure by measuring the change in capacitance of a flexible membrane attached but insulated from a conductive, gas-filled cavity due to deflections caused by pressure applied over the flexible membrane (i.e., a capacitive pressure sensor). Alternatively, pressure sensor 42 may be a sensor that utilizes the piezo-electric effect (i.e., a piezo-electric pressure sensor) or resistive change due to metallic strain (i.e., a strain gauge pressure sensor) in order to measure pressure applied.

Processor 26 of IMD 12, alone or in conjunction with a processor of programmer 20 or another device communicatively connected to IMD 12, may be configured to receive the pressure of reservoir 34 measured by pressure sensor 42. Processor 26 may then detect unexpected changes in the volume of therapeutic fluid in reservoir 34 based on changes in the pressure of the reservoir measured by pressure sensor 42 over a period of time. In one example, processor 26 detects unexpected changes in the volume of therapeutic fluid in reservoir 34 by determining a difference between an actual rate at which the therapeutic fluid is delivered from the reservoir and a rate at which the therapeutic fluid is expected to be delivered from the reservoir. In another example, processor 26 of IMD 12 detects unexpected changes in the volume of therapeutic fluid in reservoir 34 by determining a difference between an actual volume of therapeutic fluid in the reservoir and an expected volume of therapeutic fluid in the reservoir.

Processor 26 of IMD 12 may also be configured to control an ambulatory volume gauge to indicate to patient 16 or another user the volume of therapeutic fluid in reservoir 34 as the IMD delivers therapy to the patient. In one example, processor 26 is configured to determine a volume of therapeutic fluid in reservoir 34 based on changes in the pressure of the reservoir measured by pressure sensor 42 over time. Processor 26 also controls an ambulatory fluid volume gauge to indicate the determined volume of fluid in reservoir 34. In some examples, processor 26 temporarily or permanently stores the determined volume of therapeutic fluid in reservoir 34 in memory 28. In one example, the ambulatory fluid volume gauge may be a display of programmer 20, which displays a text or graphical representation of the volume of fluid in the reservoir. In another example, the ambulatory fluid volume gauge may be a separate display or display of another device, e.g. a laptop, desktop, or server computer, which is communicatively connected to IMD 12 and configured to display a text or graphical representation of the volume of fluid in the reservoir.

Periodically, fluid may need to be supplied percutaneously to reservoir 34 because all of a therapeutic fluid has been or will be delivered to patient 16, or because a clinician wishes to replace an existing fluid with a different fluid or similar fluid with different concentrations of therapeutic ingredients. Refill port 26 can therefore comprise a self-sealing membrane to prevent loss of therapeutic fluid delivered to reservoir 30 via refill port 26. For example, after a percutaneous delivery system, e.g., a hypodermic needle, penetrates the membrane of refill port 26, the membrane may seal shut when the needle is removed from refill port 26.

In general, memory 28 stores program instructions and related data that, when executed by processor 26, cause IMD 12 and processor 26 to perform the functions attributed to them in this disclosure. For example, memory 28 of IMD 12 may store instructions for execution by processor 26 including, e.g., therapy programs, programs for monitoring the volume of therapeutic fluid in reservoir 34, and any other information regarding therapy delivered to patient 16 and/or the operation of IMD 12. Memory 28 may include separate memories for storing instructions, patient information, therapy parameters, therapy adjustment information, program histories, and other categories of information such as any other data that may benefit from separate physical memory modules. Therapy adjustment information may include information relating to timing, frequency, rates and amounts of patient boluses or other permitted patient modifications to therapy.

At various times during the operation of IMD 12 to treat patient 16, communication to and from IMD 12 may be necessary to, e.g., change therapy programs, adjust parameters within one or more programs, configure or adjust a particular bolus, or to otherwise download information to or from IMD 12. Processor 26 controls telemetry module 30 to wirelessly communicate between IMD 12 and other devices including, e.g. programmer 20. Telemetry module 30 in IMD 12, as well as telemetry modules in other devices described in this disclosure, such as programmer 20, can be configured to use RF communication techniques to wirelessly send and receive information to and from other devices respectively according to, e.g., the 802.11 or Bluetooth specification sets, infrared (IR) communication according to the IRDA specification set, or other standard or proprietary telemetry protocols. In addition, telemetry module 30 may communicate with programmer 20 via proximal inductive interaction between IMD 12 and the external programmer. Telemetry module 30 may send information to external programmer 20 on a continuous basis, at periodic intervals, or upon request from the programmer.

Power source 44 delivers operating power to various components of IMD 12. Power source 44 may include a small rechargeable or non-rechargeable battery and a power generation circuit to produce the operating power. In the case of a rechargeable battery, recharging may be accomplished through proximal inductive interaction between an external charger and an inductive charging coil within IMD 12. In some examples, power requirements may be small enough to allow IMD 12 to utilize patient motion and implement a kinetic energy-scavenging device to trickle charge a rechargeable battery. In other examples, traditional batteries may be used for a limited period of time. As another alternative, an external inductive power supply could transcutaneously power IMD 12 as needed or desired.

Figure 3:
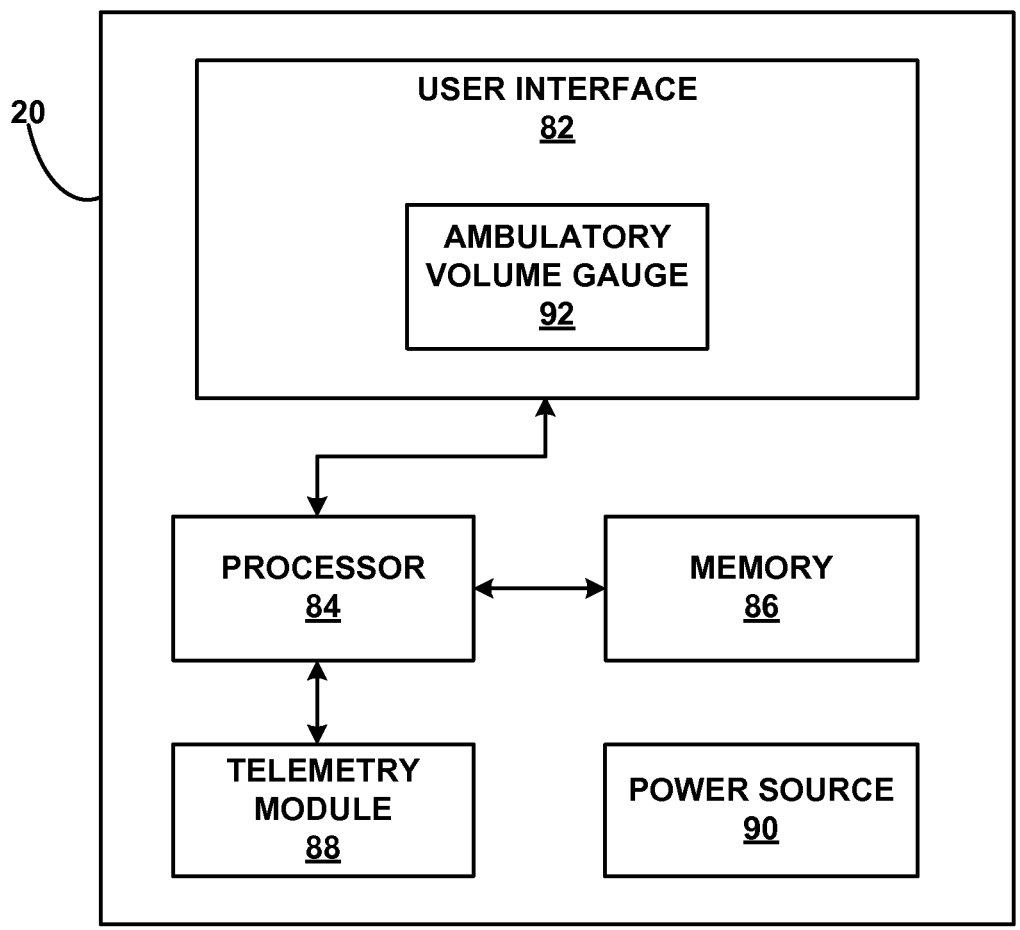
FIG. 3 is a functional block diagram illustrating an example of an external programmer shown in FIG. 1.

FIG. 3 is a functional block diagram illustrating an example of various components of external programmer 20 for IMD 12. As shown in FIG. 3, external programmer 20 may include user interface 82, processor 84, memory 86, telemetry module 88, and power source 90. A clinician or patient 16 interacts with user interface 82 in order to manually change the parameters of a therapy program, change therapy programs within a group of programs, view therapy information, view historical or establish new therapy programs, or otherwise communicate with IMD 12 or view or edit programming information. Processor 84 controls user interface 82, retrieves data from memory 86 and stores data within memory 86. Processor 84 also controls the transmission of data through telemetry module 88 to IMD 12. The transmitted data may include therapy program information specifying various therapeutic fluid delivery parameters. Memory 86 may store, e.g., operational instructions for processor 84 and data related to therapy for patient 16.

Programmer 20 may be a hand-held computing device that includes user interface 82 that can be used to provide input to programmer 20. For example, programmer 20 may include a display screen that presents information to the user and a keypad, buttons, a peripheral pointing device, touch screen, voice recognition, or another input mechanism that allows the user to navigate though the user interface of programmer 20 and provide input. In other examples, rather than being a handheld computing device or a dedicated computing device, programmer 20 may be a larger workstation or a separate application within another multi-function device.

User interface 82 may generally include a display screen or other output mechanisms and buttons or other input mechanisms that allow a user to receive information from and provide input to external programmer 20, respectively. In one example, user interface includes one or more of a touch pad, increase and decrease buttons, an emergency shut off button, and other buttons needed to control the therapy delivered to patient 16 by IMD 12. In another example, user interface 82 may additionally or only utilize a touch screen display including, e.g., a liquid crystal display (LCD), dot matrix display, organic light-emitting diode (OLED) display, touch screen, or any other device capable of delivering and/or accepting information. For visible indications of therapy program parameters or operational status, a display screen may suffice. For audible and/or tactile indications of therapy program parameters or operational status, programmer 20 may further include one or more audio speakers, voice synthesizer chips, piezoelectric buzzers, or the like.

User interface 82 may be configured to present therapy program information to the user as graphical bar graphs or charts, numerical spread sheets, or in any other manner in which information may be displayed. Further, user interface 82 may present nominal or suggested therapy parameters that the user may accept via user interface 82. User interface 82 also provides input mechanisms to enable the user to program IMD 12 in accordance with one or more therapy programs or otherwise provide data to IMD 12 necessary for delivering therapy to patient 16.

When programmer 20 is configured for use by a clinician, user interface 82 may be used to transmit initial programming information to IMD 12 including hardware information for system 10, e.g. the type of catheter 18, the position of catheter 18 within patient 16, a baseline orientation of at least a portion of IMD 12 relative to a reference point, and software information related to therapy delivery and operation of IMD 12, e.g. therapy parameters of therapy programs stored within IMD 12 or within programmer 20, the type and amount, e.g., by volume of therapeutic fluid(s) delivered by IMD 12 and any other information the clinician desires to program into IMD 12. The clinician may use programmer 20 during a programming session to define one or more therapy programs by which IMD 12 delivers therapy to patient 16, in which case patient 16 may provide feedback to the clinician during the programming session as to efficacy of a program being evaluated or desired modifications to the program. Programmer 20 may assist the clinician in the creation/identification of therapy programs by providing a methodical system of identifying potentially beneficial therapy parameters.

Programmer 20 may also be configured for use by patient 16. When configured as a patient programmer, programmer 20 may have limited functionality in order to prevent patient 16 from altering critical functions or applications that may be detrimental to patient 16. In this manner, programmer 20 may only allow patient 16 to adjust certain therapy parameters or set an available range for a particular therapy parameter. In some cases, a patient programmer may permit the patient to control IMD 12 to deliver a supplemental, patient bolus, if permitted by the applicable therapy program administered by the IMD, e.g., if delivery of a patient bolus would not violate a lockout interval or maximum dosage limit. Programmer 20 may also provide an indication to patient 16 when therapy is being delivered or when IMD 12 needs to be refilled or when the power source within programmer 20 or IMD 12 need to be replaced or recharged.

In the example of FIG. 3, user interface 82 of programmer 20, whether employed as a patient or clinician programmer, includes ambulatory volume gauge 92, which is configured to indicate the volume of therapeutic fluid in reservoir 34 of IMD 12. Whether controlled by processor 26 of IMD 12, as described above, or processor 84 of programmer 20, ambulatory volume gauge 92 is configured to display via user interface 82 the volume of therapeutic fluid in reservoir 34 that is determined based on changes in the pressure of the reservoir measured by pressure sensor 42 over time. Ambulatory volume gauge 92 may include any combination of text or graphical representations of the volume of fluid in reservoir 34. For example, ambulatory volume gauge 92 may include an iconic representation of the volume of therapeutic fluid in reservoir 34 including a series of bars that are colored, filled in, highlighted, increase and decrease in size, or otherwise vary based on the volume fluid in the reservoir. In another example, ambulatory volume gauge 92 includes a graphical representation of the circular face of a mechanical gauge with numerical or other indications of the level of fluid in reservoir 34. In another example, ambulatory volume gauge 92 includes a numerical or textual indication of the amount of fluid in reservoir 34.

Processor 84 of programmer 20 may be employed, in conjunction with or in lieu of processor 26 of IMD 12, to detect unexpected changes in the volume of therapeutic fluid in reservoir 34 based on changes in the pressure of the reservoir measured by pressure sensor 42 over a period of time. For example, IMD 12 may transmit changes in the pressure of reservoir 34 measured by pressure sensor 42 to programmer 20 via telemetry modules 30 and 82 of IMD 12 and programmer 20, respectively. Processor 84 may then employ the changes in the pressure of reservoir 34 measured by sensor 42 to detect unexpected changes in the volume of therapeutic fluid in the reservoir. Additionally, processor 26 of IMD 12 may collect and store pressure measurements made by pressure sensor 42 in memory 28. An external instrument, e.g. a patient programmer may automatically pull changes in the pressure of reservoir 34 measured by pressure sensor 42 from memory 28 via telemetry modules 30 and 82 on a regular basis. In another example, a clinician programmer may pull changes in the pressure of reservoir 34 measured by pressure sensor 42 from memory 28 via telemetry modules 30 and 82 on a patient visit. In either case, processor 86 may store the pressure changes in reservoir 34 in memory 86 and may employ the changes in pressure measured by sensor 42 to detect unexpected changes in the volume of therapeutic fluid in the reservoir.

Additionally, processor 84 of programmer 20 may be employed, in conjunction with or in lieu of processor 26 of IMD 12, to determine a volume of therapeutic fluid in reservoir 34 based on changes in the pressure of the reservoir measured by pressure sensor 42 over time and to control ambulatory fluid volume gauge 92 of user interface 82 to indicate the determined volume of fluid in reservoir 34. In some examples, processor 26 of IMD 12 determines the volume of therapeutic fluid in reservoir 34 and transmits the determined volume via telemetry module 30 to programmer 20. Processor 84 of programmer 20 may store the volume in memory 86. In other examples, however, processor 84 may query IMD 12 via telemetry module 88 to retrieve pressure measurements of reservoir 34 made by pressure sensor 42 and then determine the volume of therapeutic fluid in the reservoir based pressure changes measured by the pressure sensor. In either case, processor 84 of programmer 20 may store the volume in memory 86. In one example, as described above, ambulatory volume gauge 92 is displayed on user interface 82 of programmer 20 in the form of a text or graphical representation of the volume of fluid in the reservoir. In another example, however, an ambulatory fluid volume gauge may be a separate display or display of another device, e.g. a laptop, desktop, or server computer, which is communicatively connected to programmer 20 and configured to display a text or graphical representation of the volume of fluid in reservoir 34 of IMD 12.

Telemetry module 88 allows the transfer of data to and from programmer 20 and IMD 12, as well as other devices, e.g. according to the RF communication techniques described above with reference to FIG. 2. Telemetry module 88 may communicate automatically with IMD 12 at a scheduled time or when the telemetry module detects the proximity of IMD 12. Alternatively, telemetry module 88 may communicate with IMD 12 when signaled by a user through user interface 82. To support RF communication, telemetry module 88 may include appropriate electronic components, such as amplifiers, filters, mixers, encoders, decoders, and the like. Programmer 20 may also communicate with another programmer or computing device via a wired or wireless connection using any of a variety of communication techniques, and/or via exchange of removable media, including, e.g., magnetic or optical disks, or memory cards or sticks including, e.g., non-volatile memory. Further, programmer 20 may communicate with IMD 12 or another device via, e.g., a local area network (LAN), wide area network (WAN), public switched telephone network (PSTN), or cellular telephone network, or any other terrestrial or satellite network appropriate for use with programmer 20 and IMD 12.

Power source 90 may be a rechargeable battery, such as a lithium ion or nickel metal hydride battery. Other rechargeable or conventional primary cell batteries may also be used. In some cases, external programmer 20 may be used when coupled to an alternating current (AC) outlet, i.e., AC line power, either directly or via an AC/DC adapter.

In some examples, external programmer 20 may be configured to recharge IMD 12 in addition to programming IMD 12. Alternatively, a recharging device may be capable of communication with IMD 12. Then, the recharging device may be able to transfer programming information, data, or any other information described herein to IMD 12. In this manner, the recharging device may be able to act as an intermediary communication device between external programmer 20 and IMD 12.

Figure 4:
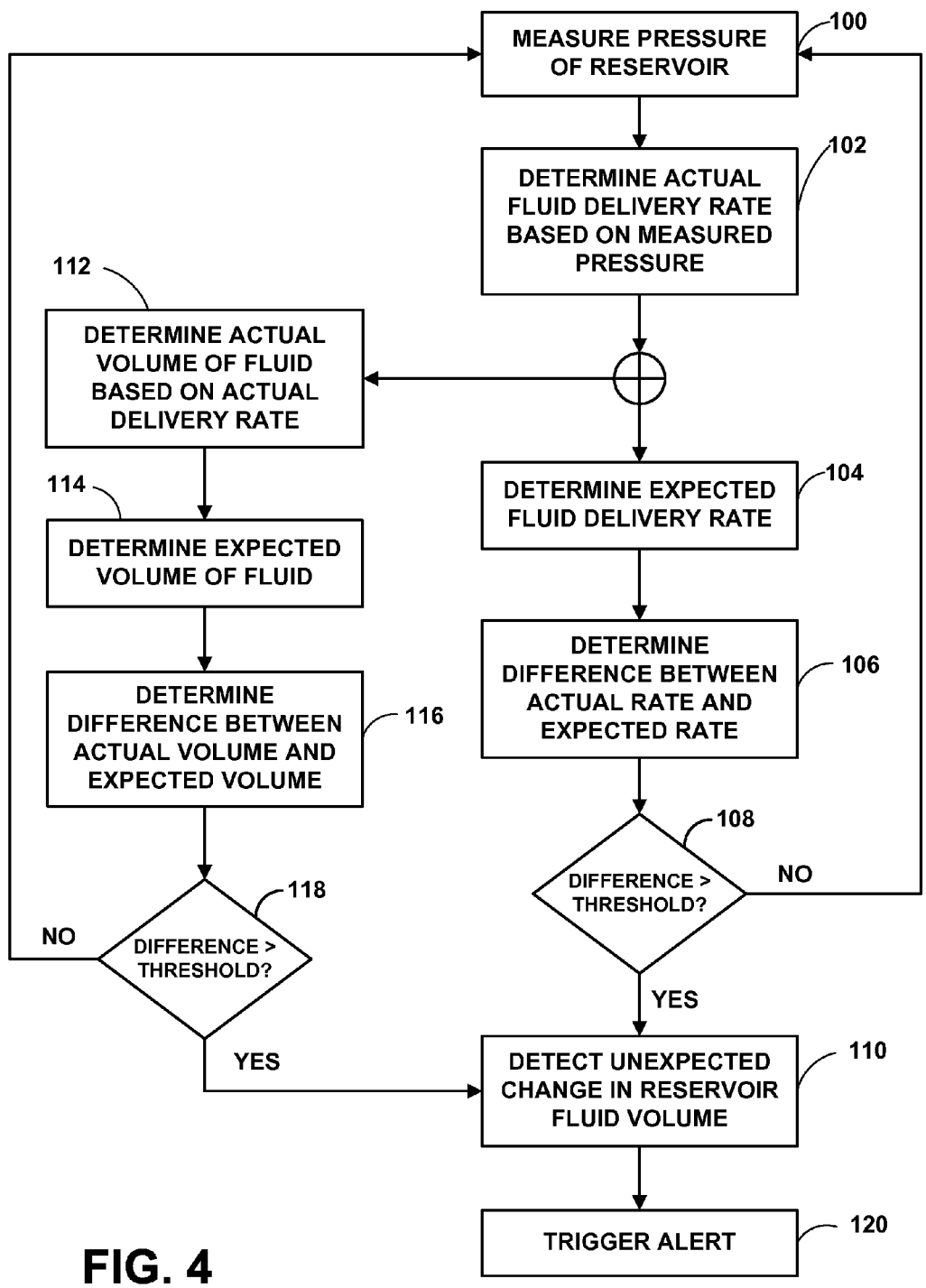
FIG. 4 is a flow chart illustrating an example method of detecting unexpected changes in the volume of therapeutic fluid in a reservoir of an implantable fluid delivery device.

FIG. 4 is a flow chart illustrating an example method of detecting unexpected changes in the volume of therapeutic fluid in the reservoir of an IMD based on changes in the pressure of the reservoir measured over a period of time by a pressure sensor. The method of FIG. 4 includes measuring the pressure of the reservoir of an IMD (100) and determining the actual rate at which therapeutic fluid is delivered from the reservoir based on changes in the pressure of the reservoir measured by the pressure sensor over a period of time (102). The method of FIG. 4 also includes determining a rate at which the therapeutic fluid is expected to be delivered from the reservoir (104), determining a difference between the actual rate and the expected rate of fluid delivery (106), and detecting an unexpected change in the volume of therapeutic fluid in the reservoir (110) if the difference between the actual rate and the expected rate of fluid delivery is greater than a threshold (108). The unexpected change may be indicative of fluid leakage, unauthorized removal of fluid, or other anomaly.

In some examples, the method of FIG. 4 optionally includes determining the actual volume of fluid in the reservoir of the IMD based on the actual fluid delivery rate (112). In such examples, the method of FIG. 4 also includes determining a volume of fluid expected to be in the reservoir (114), determining a difference between the actual reservoir fluid volume and the expected reservoir fluid volume (116), and detecting an unexpected change in the volume of therapeutic fluid in the reservoir (110) if the difference between the actual reservoir fluid volume and the expected reservoir fluid volume is greater than a threshold (118). Regardless of the manner in which the change is detected, the method of FIG. 4 may include triggering an alert (120) if an unexpected change in reservoir fluid volume is detected.

The functions of the method of FIG. 4 for detecting unexpected changes in volume of therapeutic fluid in the reservoir of an IMD are described as executed by IMD 12, and in particular, processor 26 and memory 28 of IMD 12. However, in other examples, one or more of these functions may be carried out by other devices including, e.g., external programmer 20. For example, unexpected changes in the volume of therapeutic fluid in reservoir 34 may be detected by processor 84 of programmer 20 and stored on memory 86. Alternatively, one or more of the functions associated with the method of FIG. 4 may be executed by processor 84 of programmer 20, while the remaining functions are executed by processor 26 of IMD 12. Other combinations of distributing the execution functions of the method of FIG. 4 among a number of devices to detect unexpected changes in the reservoir fluid volume of IMD 12 are possible, including employing external devices communicatively connected to IMD 12 other than programmer 20 to execute one or more of the functions of the method of FIG. 4.

The method of FIG. 4 includes measuring the pressure of reservoir 34 of IMD 12 (100). In one example, processor 26 of IMD 12 controls pressure sensor 42 to measure the pressure in reservoir 34. Generally speaking, processor 26 may detect unexpected changes in the volume of therapeutic fluid in reservoir 34 based on changes in the pressure of the reservoir measured by pressure sensor 42 over time. The manner in which processor 26 detects the unexpected reservoir fluid volume changes based on changes in the pressure of the reservoir may vary.

As represented in steps 102-110 of the example method of FIG. 4, unexpected reservoir fluid volume changes may be detected based on the difference between an actual rate and an expected rate at which fluid is delivered from reservoir 34. As represented in steps 102, 112-118 and 110 of FIG. 4, unexpected reservoir fluid volume changes may be additionally or alternatively detected based on the difference between an actual and an expected volume of the therapeutic fluid in reservoir 34. In either case, however, processor 26 of IMD 12 determines the actual rate at which therapeutic fluid is delivered from reservoir 34 based on changes in the pressure of the reservoir measured by pressure sensor 42 over a period of time (102).

In one example, processor 26 may determine the actual rate at which the therapeutic fluid is delivered from reservoir 34 (102) by, e.g., dividing a change in the pressure, $\Delta P_R$, of the reservoir measured by pressure sensor 42 over a time period by a constant, $K_v$, representing the sensitivity of the pressure of the reservoir to changes in the volume of therapeutic fluid in the reservoir according to the following formula.

$$r_{actual} = \frac{\Delta P_R}{\Delta t \cdot K_v}$$

As illustrated by this formula, the actual rate at which the therapeutic fluid is delivered from reservoir 34 corresponds to the slope of the pressure profile of the reservoir over time. The pressure sensitivity to volume constant, $K_v$, is a characteristic of reservoir 34 of IMD 12 that behaves like a spring, e.g. in cases where the reservoir is formed as a resilient bellows, in which the spring constant or characteristic, $K_v$, represents the amount of incremental change in pressure in the reservoir per incremental change in volume of fluid in the reservoir. In other words, $K_v$ is approximately equal to $\Delta P_R/\Delta V$, where V is equal to the volume of therapeutic fluid in reservoir 34. In some examples, before determining the actual rate at which the therapeutic fluid is delivered from reservoir 34, it may be necessary for processor 26 to normalize the change in the pressure of reservoir 34 measured by pressure sensor 42 for temperature variations that cause short term pressure fluctuations inconsistent with a longer term downward pressure trend caused by the decreasing fluid volume in the reservoir.

Figure 5:
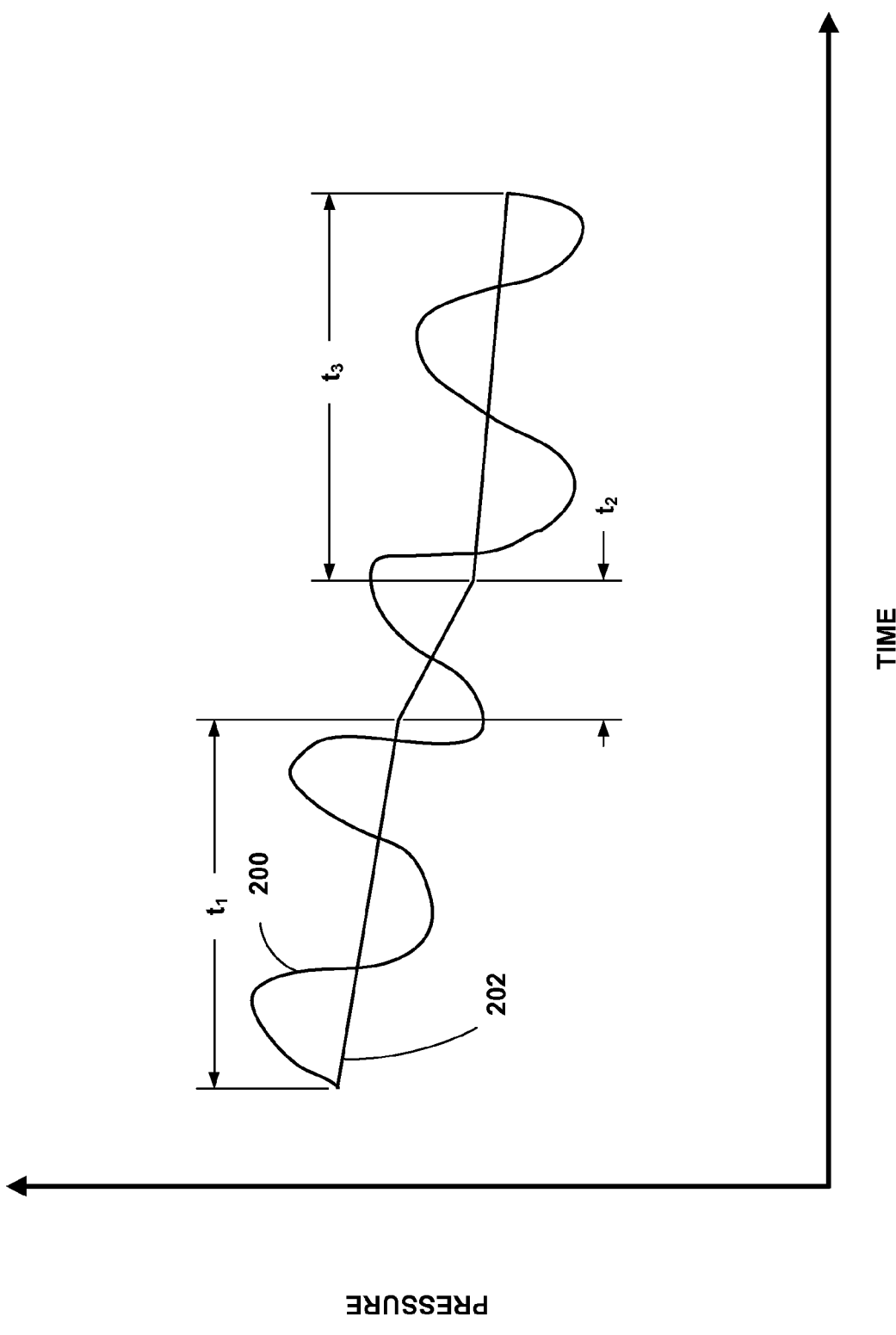
FIG. 5 is a graph illustrating the pressure of a reservoir of a fluid delivery device measured by a pressure sensor over time.

FIG. 5 is a graph illustrating the pressure of reservoir 34 measured by pressure sensor 42 over time as processor 26 controls pump 32 to deliver therapeutic fluid to patient 16. In FIG. 5, curve 200 is fit to a number of values of the pressure of reservoir 34 measured by pressure sensor 42 over time. The pressure of reservoir 34 will exhibit both shorter and longer term trends as processor 26 controls pump 32 to deliver therapeutic fluid to patient 16. Over the course of a relatively short period of time, e.g. a few hours up to a twenty-four hour period, the pressure of reservoir 34 may rise and fall even though the volume of therapeutic fluid in the reservoir is consistently dropping.

Non-linear variations in the pressure of reservoir 34 inconsistent with the general linear trend of decreasing fluid volume of the reservoir according to a programmed delivery rate may be caused by short term fluctuations in the temperature of the reservoir, which, in turn, may be caused by fluctuations in the body temperature of patient 16. In some examples, as illustrated in FIG. 5, the pressure of reservoir 34 over a given period of time, e.g. a twenty-four hour period, may exhibit a sinusoidal swing between increasing reservoir pressures and decreasing reservoir pressures. Such short term pressure variations in reservoir 34 may be caused by changes in the temperature of the body of patient 16 as a function of the circadian rhythm of the patient. Over longer periods of time, e.g. one or more twenty-four hour periods, the sinusoidal variations in the pressure of reservoir 34 measured by pressure sensor 42 will trend down as the volume of therapeutic fluid in the reservoir decreases.

The short term temperature effects on the pressure of reservoir 34 may not, in some examples, be meaningful to detecting unexpected changes in the volume of therapeutic fluid of the reservoir. Additionally, the short term temperature effects on the pressure of reservoir 34 may complicate the determination of the actual rate at which the therapeutic fluid is delivered from the reservoir to the point of impracticality. Therefore, in one example, the change in the pressure of reservoir 34 measured by pressure sensor 42 over time may be normalized for temperature changes to determine an average change in the pressure of the reservoir over time to filter out short term pressure variations caused by temperature fluctuations while retaining the longer term drop in the pressure of the reservoir as fluid is delivered to patient 16.

Because of the relatively large swing in pressure values sensed by pressure sensor 42 caused by temperature changes in reservoir 34, the long term pressure trend in the reservoir cannot be determined by simply averaging a number of pressure values measured by the pressure sensor. Therefore, in some examples, a linear regression may be performed on the sinusoidal temperature dependent pressure of reservoir 34 represented in FIG. 5 by curve 200 to determine the long term pressure trend, from which unexpected changes in reservoir fluid volume may be detected and/or an ambulatory fluid volume gauge may be controlled (as will be described below with reference to the example method of FIG. 7). The change in the pressure of reservoir 34 normalized for temperature changes is illustrated in FIG. 5 as curve 202, which is a linear regression of the pressure of reservoir 34 measured by pressure sensor 42 over time.

In order to determine the long term pressure trend of reservoir 34 based on the temperature dependent pressure measurements made by pressure sensor 42, in one example, processor 26 of IMD 12 may perform a least squares linear regression on the pressure values measured by the pressure sensor. With reference to the data represented in FIG. 5, therefore, processor 26 may perform a least squares linear regression on curve 200 to determine curve 202. In one example, processor 26 determines the long term pressure trend in reservoir 34 by performing a least squares linear regression on the pressure values measured by pressure sensor 42 according to the following formula.

$$\frac{\Delta P}{\Delta t} = \frac{\sum (t_k \cdot P_k) - \frac{1}{N} \cdot \sum P_k \cdot \sum t_k}{\sum (t_k)^2 - \frac{1}{N} \cdot (\sum t_k)^2}$$

In the foregoing formula, the rate of change of pressure over time, $\Delta P/\Delta t$, in reservoir 34 is determined based on the time, $t_k$, at pressure measurement k by pressure sensor 42, the pressure, $P_k$, at measurement k by the pressure sensor, and the number of temperature affected cycle peaks, N, sampled by the pressure sensor up to measurement k. The number of cycle peaks, N, generally corresponds to the number of maximum and minimum pressure values measured by pressure sensor 42 over the sampling period including k samples. For example, in FIG. 5, over all of the time periods, $t_1$, $t_2$, and $t_3$, there are a total of eight maximum and minimum pressure values.

In view of the relationships between reservoir pressure and temperature illustrated in FIG. 5, in one example, processor 26 may determine the actual rate, $r_{actual}$, at which the therapeutic fluid is delivered from reservoir 34 (102) by dividing the rate of change of pressure of the reservoir measured by pressure sensor 42 over time, $\Delta P/\Delta t$, determined using the foregoing least squares method by the pressure sensitivity to volume change constant, $K_v$, according to the following formula.

$$r_{actual} = \frac{\left[\frac{\sum (t_k \cdot P_k) - \frac{1}{N} \cdot \sum P_k \cdot \sum t_k}{\sum (t_k)^2 - \frac{1}{N} \cdot (\sum t_k)^2}\right]}{K_v}$$

$$= \frac{\Delta P}{\Delta t \cdot K_v}$$

In order to normalize the change in the pressure of reservoir 34 for temperature variations, pressure sensor 42 needs to measure a sufficient number of data points to capture the shorter term pressure variation trend, e.g. the sinusoidal trend illustrated by curve 200 in FIG. 5. In some examples, therefore, the period of time over which pressure sensor 42 measures changes in the pressure of reservoir 34 may be limited by processor 26 to a minimum period of time, e.g. stored in memory 28. In one example, processor 26 may require pressure sensor 42 to measure changes in the pressure of reservoir 34 for at least one twenty-four hour period before normalizing the pressure changes for temperature changes.

Although the foregoing example has been described with reference to normalizing the change in the pressure of reservoir 34 measured by pressure sensor 42 for temperature variations numerically, in other examples, temperature effects may be accounted for by other methods. For example, IMD 12 may employ a temperature sensor to measure temperatures in reservoir 34. Temperature sensors appropriate for use in IMD 12 may include, e.g., a sensor in which a voltage drop across a diode that is conducting a known, constant current provides a know relationship to a semiconductor's temperature, which, in turn corresponds to the temperature of reservoir 34. In another example, a resistive temperature detector (RTD), which employs one or more metal alloys that alter their electrical resistance relative to temperature. Thermocouple devices provide another example of a temperature sensor for use with IMD 12 to directly sense the temperature of reservoir 34. Thermocouples are configured with a junction between two different metals that produces a voltage related to a temperature difference of the two metals at the junction. Based on the changing temperatures measured by the temperature sensor, processor 26 of IMD 12 may, e.g., automatically adjust each pressure measurement of pressure sensor 42 for the temperature swings. Whatever the particular pressure adjustment method, a temperature sensor may be employed to directly account for temperature changes in reservoir 34 that also affect pressure and fluid volume changes in the reservoir.

The method of FIG. 4 also includes determining a rate at which the therapeutic fluid is expected to be delivered from the reservoir (104). The expected fluid delivery rate will generally be a known value that is a function of a therapy program stored on memory 28 and executed by processor 26 to cause pump 32 to deliver the therapeutic fluid from reservoir 34 to patient 16. In this sense, determining the expected fluid delivery rate (104) may generally include processor 26 retrieving a programmed rate stored on memory 28. As noted above, however, processor 26 of IMD 12 may be programmed to deliver a dose of therapeutic fluid to patient 16 according to a schedule that defines different fluid delivery rates at different times during the dose period, e.g. a twenty-four hour period. In such examples in which IMD 12 is programmed to delivery fluid at different rates within the relevant time period, determining the expected fluid delivery rate (104) may include processor 26 retrieving a number of programmed rates for the time period from memory 28 and calculating an average expected fluid delivery rate based on the retrieved rates and the proportion of the time period over which they are programmed to be delivered.

In addition to determining the expected fluid delivery rate (104), the method of FIG. 4 also includes determining a difference between the actual rate and the expected rate of fluid delivery (106) and detecting an unexpected change in the volume of therapeutic fluid in the reservoir (110) if the difference between the actual rate and the expected rate of fluid delivery is greater than a threshold (108). Processor 26 of IMD 12 may, for example, determine the difference between the actual and the expected fluid delivery rate (106) by retrieving the rates from memory 28 and subtracting them from one another. Processor 26 may then compare the difference between the actual, $r_{actual}$, and the expected, $r_{expected}$, fluid delivery rate to a threshold, e.g. stored on memory 28. If the difference between the actual rate and the expected rate of fluid delivery from reservoir 34 is greater than a threshold, processor 26 may be programmed to indicate that an unexpected change in fluid volume has been detected. The difference calculation by processor 26 of the actual and the expected fluid delivery rate and the threshold to which it is compared may be an absolute difference, $r_{deviation}$, in fluid delivery rates or a percentage change, $r_{error}$, from the expected to the actual according to the following formulas.

$$r_{deviation} = r_{actual} - r_{expected}$$

$$r_{error} = \left[\frac{r_{actual} - r_{expected}}{r_{expected}}\right] \cdot 100\%$$

Referring again to FIG. 5, the change in the pressure of reservoir 34 normalized for temperature changes illustrated as curve 202 also illustrates a possible unexpected change in the volume of fluid in the reservoir. The pressure of reservoir 34 measured by pressure sensor 42 illustrated in the graph of FIG. 5 spans three time periods $t_1$, $t_2$, $t_3$, as processor 26 controls pump 32 to deliver therapeutic fluid to patient 16. IMD 12 delivers the therapeutic fluid to patient 16 for the first time period $t_1$ and the pressure of reservoir 34 as measured by pressure sensor 42 steadily declines an approximately constant rate. Similarly, IMD 12 delivers the therapeutic fluid to patient 16 for the third time period $t_3$ and the pressure of reservoir 34 as measured by pressure sensor 42 steadily declines an approximately constant rate. The steady decline in pressure and corresponding decline in volume of fluid in reservoir 34 of IMD 12 during time periods $t_1$ and $t_3$, although being steady and constant or nearly constant, may deviate from the expected pressure decline and may, therefore, signal an unexpected change in the volume of therapeutic fluid in the reservoir. In some examples, such a steady decline in pressure and volume in reservoir 34 beyond what is expected based on delivery of the therapeutic fluid to patient 16 may be caused by a malfunction in IMD 12. For example, the drop in pressure and corresponding depletion of fluid in reservoir 34 during time periods $t_1$ an $t_3$ may be caused not only by delivery of the fluid to patient 16, but also by a leak in a valve of pump delivery pump 32 of IMD 12.

In contrast to time periods $t_1$ and $t_3$, during time period $t_2$, pressure sensor 42 detects a steep decline in the pressure of reservoir 34. The rapid decline in pressure in reservoir 34 measured by pressure sensor 42 during time period $t_2$ may signal an unexpected change in the volume of therapeutic fluid in the reservoir. The nearly step-wise pressure drop illustrated in the time period $t_2$ in FIG. 5 may be caused, e.g., by patient 16 or another unauthorized person removing therapeutic fluid from reservoir 34, e.g., via a hypodermic needle inserted into refill port 36 or catheter access port 40.

The threshold to which processor 26 compares the difference between the actual rate and the expected rate of fluid delivery from reservoir 34 to detect an unexpected change in therapeutic fluid volume may vary over time such that as the period of time over which pressure sensor 42 measures changes in the pressure of the reservoir increases the threshold decreases. The variation of the threshold over time accounts for the increased accuracy with which unexpected changes in reservoir fluid volume can be detected by processor 26 based on pressure changes measured by pressure sensor 42 as more pressure data is gathered by the sensor over time. For example, over one twenty-four hour period of pressure changes in reservoir 34 measured by pressure sensor 42, the percentage threshold deviation between actual and expected fluid delivery rate may be approximately +−500%, meaning that processor 26 may detect unexpected volume changes for actual fluid deliver rates that deviate from the expected rate by greater than or equal to +−500%. After four twenty-four hour periods of pressure changes in reservoir 34 measured by pressure sensor 42, the percentage threshold deviation between actual and expected fluid delivery rate may be approximately +−100%, meaning that processor 26 may detect unexpected volume changes for actual fluid deliver rates that deviate from the expected rate by greater than or equal to +−100%. After five twenty-four hour periods of pressure changes in reservoir 34 measured by pressure sensor 42, the percentage threshold deviation between actual and expected fluid delivery rate may be approximately +−25%, meaning that processor 26 may detect unexpected volume changes for actual fluid deliver rates that deviate from the expected rate by greater than or equal to +−25%. Finally, after seven twenty-four hour periods of pressure changes in reservoir 34 measured by pressure sensor 42, the percentage threshold deviation between actual and expected fluid delivery rate may be approximately +−12%, meaning that processor 26 may detect unexpected volume changes for actual fluid deliver rates that deviate from the expected rate by greater than or equal to +−12%.

Figure 6:
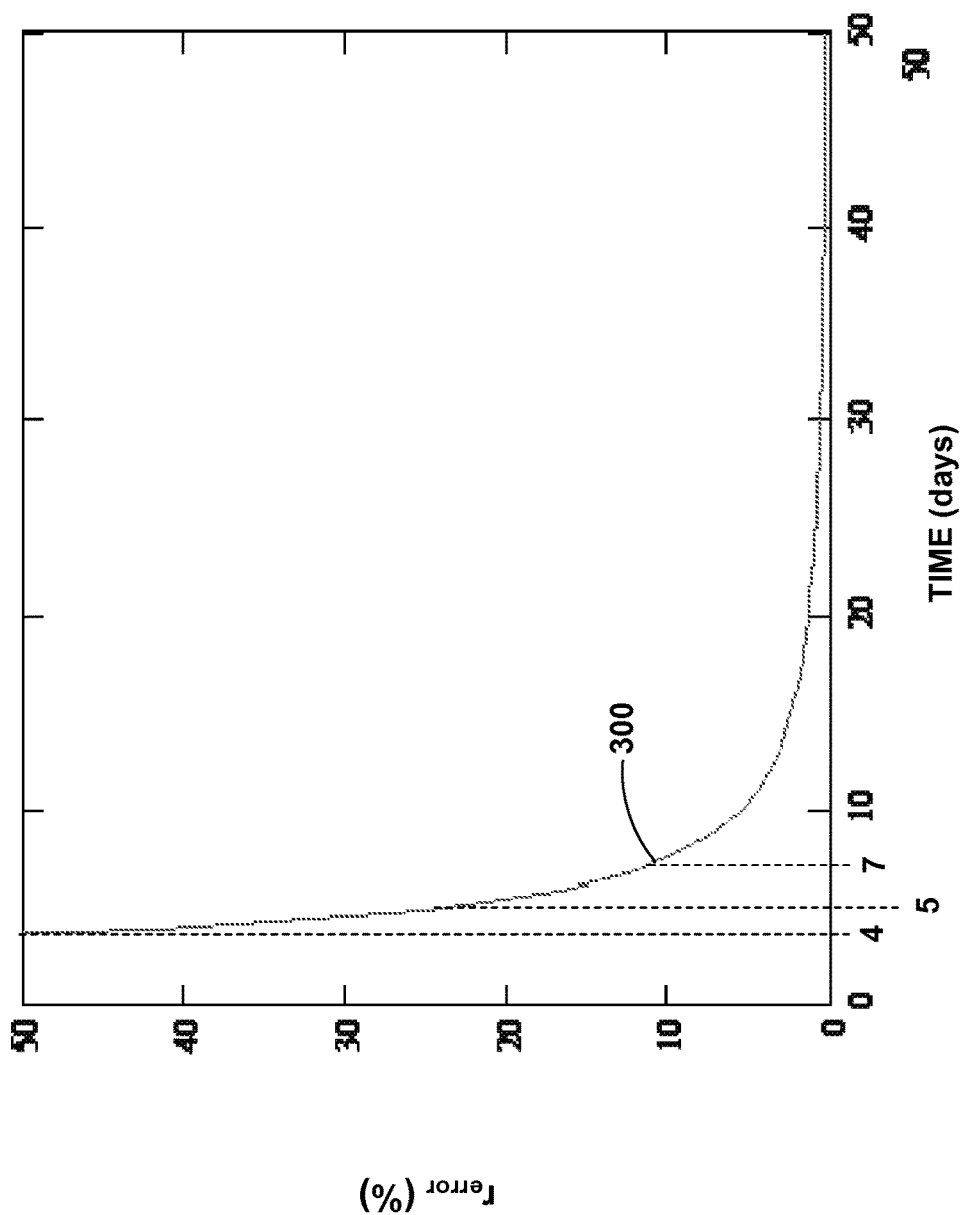
FIG. 6 is a graph illustrating the threshold change between expected and actual fluid volume delivery rates detectable by a processor over a period of time over which a pressure sensor measures the pressure of a reservoir of a fluid delivery device.

The relationship between the period of time over which pressure sensor 42 measures the pressure of reservoir 34 and the threshold change between expected and actual fluid volume delivery rate detectable by processor 26 may more generally be described as an inverse square relationship. In other words, the threshold change between expected and actual fluid volume delivery rate detectable by processor 26 is inversely proportional to the square of the time over which pressure sensor 42 measures the pressure of reservoir 34. The relationship between threshold change and sensing time is illustrated in FIG. 6, which is a graph of percentage change, $r_{error}$, from the expected to the actual fluid delivery rate over time in a number of days. In FIG. 6, curve 300 illustrates the foregoing threshold limits on processor 26 comparing the difference between the actual rate and the expected rate of fluid delivery from reservoir 34. In particular, the percentage change, $r_{error}$, from the expected to the actual fluid delivery rate at days 4, 5 and 7 are illustrated in FIG. 6. In some examples, the accuracy with which fluid delivery pump 32 of IMD 12 may deliver fluid to patient 16 may be approximately +−10%, such that percentage changes, $r_{error}$, from the expected to the actual fluid delivery rate that are less than +−10% may not add any meaningful information to the detection of unexpected fluid volume changes in reservoir 34.

In other examples, the magnitude of the threshold to which processor 26 compares the difference between the actual rate and the expected rate of fluid delivery from reservoir 34 to detect an unexpected change in therapeutic fluid volume may vary not only by time, but by other factors. For example, the threshold difference between actual and expected fluid delivery rate may be adaptively set depending on the type of device or operational errors that processor 26 is configured to detect. For example, some valve leaks in fluid delivery pump 32 of IMD 12 may exhibit a +−500% fluid delivery rate deviation from the expected, meaning that the threshold difference between actual and expected fluid delivery rate may be set to a relatively high value to detect such a failure. In some examples, the threshold difference between actual and expected fluid delivery rate may be set to balance the magnitude of the threshold with the amount of sampling data that is required to achieve the threshold. For example, the threshold may be set sufficiently low, e.g. +−50%, such that processor 26 may detect unexpected volume changes in reservoir 34 caused by a majority of types of device or operational errors, but not too low so as to require an extraordinarily large number pressure measurements by pressure sensor 42 over a number of twenty-four hour periods.

Referring to the method of FIG. 4 again, as noted above, in addition to or in lieu of detecting unexpected reservoir fluid volume changes based on the difference between the actual and the expected fluid delivery rate, an unexpected reservoir fluid volume change may be detected by processor 26 based on the difference between an actual and an expected volume of the therapeutic fluid in reservoir 34. It may be necessary to compare actual and expected fluid volumes instead of fluid delivery rates, because, e.g., the rate at which fluid is expected to be delivered from reservoir 34 to patient 16 may be unavailable or unreliable. For example, the programmed fluid delivery rate stored in memory 28 may be corrupted, while a therapeutic fluid dose stored on memory 28 representing the total volume of fluid delivered over a particular period of time may be intact. In any event, as represented in steps 102, 112-118 and 110 of FIG. 4, unexpected reservoir fluid volume changes may be detected by processor 26 of IMD 12 based on the difference between an actual and an expected volume of the therapeutic fluid in reservoir 34.

The method of FIG. 4 optionally includes determining the actual volume of fluid in the reservoir of the IMD based on the actual fluid delivery rate (112). Processor 26 determines the actual rate at which therapeutic fluid is delivered from reservoir 34 to patient 16 based on changes in the pressure of the reservoir measured by pressure sensor 42 in the manner described above with reference to step 102 of the method of FIG. 4. As described above, generally speaking, processor 26 may determine the actual rate at which the therapeutic fluid is delivered from reservoir 34 by, e.g., dividing a change in the pressure, $\Delta P_R$, of the reservoir measured by pressure sensor 42 over a time period by a constant, $K_v$, representing the sensitivity of the pressure of the reservoir to changes in the volume of therapeutic fluid in the reservoir.

Processor 26 may then multiply the actual fluid delivery rate by the time period over which the changes in the pressure of reservoir 34 are measured by pressure sensor 42 to determine the actual volume of therapeutic fluid delivered from the reservoir over the time period. Processor 26 may determine the actual volume of therapeutic fluid in reservoir 34 by subtracting the actual volume of therapeutic fluid delivered from the reservoir over the time period from a starting volume of therapeutic fluid in the reservoir. The starting volume is generally a known value retrieved by processor 26 from memory 28, which may, e.g., correspond to an actual volume of therapeutic fluid in reservoir 34 determined in a previous iteration of the method of FIG. 4 or to a known amount of fluid in the reservoir after a fill or refill operation.

In addition to determining the actual volume of fluid in the reservoir of the IMD based on the actual fluid delivery rate (112), the method of FIG. 4 includes determining a volume of fluid expected to be in the reservoir (114). In general, the expected volume of therapeutic fluid in reservoir 34 during fluid delivery to patient 16 is a function of the therapy program or programs according to which IMD 12 delivers the fluid to patient 16. For example, given a known starting volume of fluid when reservoir 34 of IMD 12 is filled, the expected volume at some time after filling will be the starting volume minus the total dose of fluid programmed to be delivered over that period of time. As explained above, the expected fluid dose defined by the programming of IMD 12 may include a number of different doses delivered at different times or over different periods of times, one or more of which may be delivered at different rates.

The fluid dose expected to be delivered over the relevant period of time may be determined in a number of ways by processor 26 of IMD 12 in conjunction with therapy program data stored on memory 28. For example, the dose of fluid may be determined by multiplying the number of strokes of pump 32, which may be tracked by processor 26 and stored on memory 28, by a volume of fluid pumped per stroke, which is a fixed value based on the physical configuration of the pump. In another example, the fluid dose programmed to be delivered to patient 16 by IMD 12 over the relevant period of time corresponds to the rate at which the fluid is programmed to be delivered during that time multiplied by the time period. In another example, processor 26 of IMD 12 is programmed to control pump 32 to deliver fluid to patient 16 at more than one rate during the relevant time period, in which case the fluid dose expected to be delivered to the patient over the period of time corresponds to an average of the different programmed rates multiplied by the time period.

The method of FIG. 4 may also include determining a difference between the actual volume and the expected volume of therapeutic fluid in reservoir 34 (116) and detecting an unexpected change in the volume of therapeutic fluid in the reservoir (110) if the difference between the actual and the expected reservoir fluid volume is greater than a threshold (118). Processor 26 of IMD 12 may, for example, determine the difference between the actual and the expected reservoir fluid volume (116) by retrieving the respective volumes from memory 28 and subtracting them from one another. Processor 26 may then compare the difference between the actual and the expected reservoir fluid volume to a threshold, e.g. also stored on memory 28. If the difference between the actual volume and the expected volume of fluid in reservoir 34 is greater than a threshold, processor 26 may be programmed to indicate that an unexpected change in fluid volume has been detected, e.g., as a result of unauthorized removal of fluid by a person or as a result of leakage. As described above, the threshold to which processor 26 compares the difference between the actual and the expected reservoir fluid volume may vary over time such that as the period of time over which pressure sensor 42 measures changes in the pressure of reservoir 34 increases the threshold decreases.

Regardless of exactly how the change is detected, the method of FIG. 4 includes triggering an alert (120) if an unexpected change in the volume of therapeutic fluid in reservoir 34 is detected (110). Alerts may be triggered by processor 26, or another component of IMD 12 or another device, e.g. programmer 20, and may generally include audible, tactile, and/or visual alerts. For example, an unexpected reservoir fluid volume change alert may include audible alerts issued by programmer 20 or another external device associated with therapy system 10, in response to detection of an unexpected change by programmer 20 or detection of an alert signal sent by telemetry from IMD 12. In another example, the triggered alert includes IMD 12 vibrating within the body of patient 16, thereby providing a tactile alert. In another example, processor 26 may be configured to prompts external programmer 20, or another display device incorporated in or communicatively connected to IMD 12, to display a graphic to patient 16, thereby providing a visual alert. Other visual alerts may include text or graphical messages delivered to patient 16 and/or a clinician via text message, e-mail or other electronic communication from programmer 20 or another electronic device communicatively connected to IMD 12 and/or programmer 20.

Figure 7:
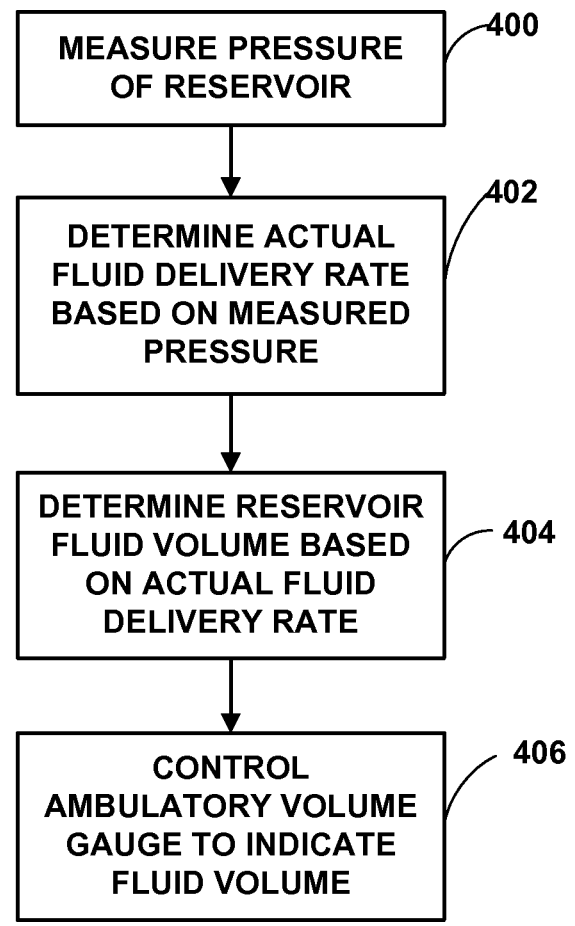
FIG. 7 is a flow chart illustrating an example method of controlling an ambulatory reservoir fluid volume gauge based on changes in the pressure of a reservoir of a fluid delivery device.

FIG. 7 is a flow chart illustrating an example method of controlling an ambulatory reservoir fluid volume gauge based on changes in the pressure of a reservoir of a fluid delivery device measured over a period of time by a pressure sensor. The method of FIG. 7 includes measuring the pressure of the reservoir of an IMD (400) and determining the actual rate at which therapeutic fluid is delivered from the reservoir based on changes in the pressure of the reservoir measured by the pressure sensor over a period of time (402). The actual volume of fluid in the reservoir is determined based on the actual rate at which therapeutic fluid is delivered from the reservoir (404). An ambulatory fluid volume gauge is controlled to indicate the actual volume of therapeutic fluid in the reservoir (406).

As with the method of FIG. 4, the functions of the method of FIG. 7 for controlling an ambulatory reservoir fluid volume gauge are described as executed by IMD 12, and in particular, processor 26 and memory 28 of IMD 12. However, in other examples, one or more of these functions may be carried out by other devices including, e.g., external programmer 20. Additionally, although ambulatory volume gauge 92 of programmer 20 of FIG. 3 is used in the description of the method of FIG. 7, other volume gauges on other devices may also be employed in conduction with examples according to this disclosure.

The method of FIG. 7 includes measuring the pressure of reservoir 34 of IMD 12 (400). In one example, processor 26 of IMD 12 controls pressure sensor 42 to measure the pressure in reservoir 34. Pressure sensor 42 samples the pressure in reservoir 34 over a period of time such and processor 26 determines the actual rate at which therapeutic fluid is delivered from reservoir 34 over the period of time (402). Determining the actual rate at which therapeutic fluid is delivered from reservoir 34 based on changes in the pressure of the reservoir measured by pressure sensor 42 over the period of time (402) may be accomplished in substantially the same manner as described above with reference to the method of FIG. 4.

For example, processor 26 may record a number of pressure values of reservoir 34 measured by pressure sensor 34 such that a short term and longer term pressure trend in the reservoir is at least partially represented. Thereafter, processor 26 may perform a linear regression on the pressure values of reservoir 34 measured by pressure sensor 42 to determine a long term pressure trend in the reservoir in the form of the rate of change of pressure, $\Delta P/\Delta t$, of the reservoir over the period of time. In one example, processor 26 may employ a least squares linear regression, as described above with reference to FIG. 4, to determine the rate of change of pressure, $\Delta P/\Delta t$, of the reservoir over the period of time. Thereafter, processor 26 may determine the actual rate at which the therapeutic fluid is delivered from reservoir 34 (402) by dividing the rate of change of pressure of the reservoir measured by pressure sensor 42 over time, $\Delta P/\Delta t$, determined using the foregoing least squares method by the pressure sensitivity to volume change constant, $K_v$.

After determining the actual rate at which the therapeutic fluid is delivered from reservoir 34 (402), the actual volume of fluid in the reservoir is determined based on the actual rate at which therapeutic fluid is delivered from the reservoir (404). In one example, the volume of therapeutic fluid delivered to patient 16 from reservoir 34, $\Delta V_R$, over the period of time may generally be calculated by processor 26 by integrating the volumetric rate, r, at which therapeutic fluid is delivered from the reservoir over time, t, according to the following formula.

$$\Delta V_R = \int_{start}^{end} r_{actual}\, dt$$

In practice, the volume of fluid delivered from reservoir 34, $\Delta V_R$, may be determined (104) by processor 26 executing the numerical equivalent of integrating the calculated rate at which therapeutic fluid is added to the reservoir, r, over the time period during which pressure is sensed by pressure sensor 42 in accordance with the following formula.

$$\Delta V_R = \sum_{start}^{end} r_{actual}\, \Delta t$$

In some examples, the actual volume of therapeutic fluid in reservoir 34, $V_R$, may be calculated by subtracting the volume of fluid delivered from reservoir 34, $\Delta V_R$, from a volume of fluid in the reservoir at the beginning of the sampling period. For example, processor 26 may subtract the volume of fluid delivered from reservoir 34, $\Delta V_R$, from an initial or starting volume of therapeutic fluid in reservoir 34 stored in memory 28. In one example, the initial or starting volume may be the volume of fluid in reservoir 34 at the point in time when the reservoir is initially filled with additional amounts of the same therapeutic fluid or filled with another fluid.

In addition to determining the actual volume of fluid in the reservoir based on the actual rate at which therapeutic fluid is delivered from the reservoir (404), processor 26 may control ambulatory fluid volume gauge 92 on user interface 82 of programmer 20 to indicate the actual volume of therapeutic fluid in the reservoir (406). For example, processor 26, alone or in conjunction with processor 84 of programmer 20, may control ambulatory volume gauge 92 via telemetry module 30 to indicate the actual volume of therapeutic fluid in reservoir 34 via text or graphical representations of the volume of fluid in reservoir. For example, ambulatory volume gauge 92 may include an iconic representation of the volume of therapeutic fluid in reservoir 34 including a series of bars that are colored, filled in, highlighted, increase and decrease in size, or otherwise vary based on the volume fluid in the reservoir. In another example, ambulatory volume gauge 92 includes a graphical representation of the circular face of a mechanical gauge with numerical or other indications of the level of fluid in reservoir 34. In another example, ambulatory volume gauge 92 includes a numerical or textual indication of the amount of fluid in reservoir 34.

Although the target therapy delivery site described with reference to the foregoing examples is proximate to the spinal cord of a patient, other applications of therapy systems in accordance with this disclosure include alternative delivery sites. In some examples, the target delivery site may be proximate to different types of tissues including, e.g., nerves, e.g. sacral, pudendal or perineal nerves, organs, muscles or muscle groups. In one example, a catheter may be positioned to deliver a therapeutic fluid to a deep brain site or within the heart or blood vessels. Delivery of a therapeutic fluid within the brain may help manage a number of disorders or diseases including, e.g., chronic pain, diabetes, depression or other mood disorders, dementia, obsessive-compulsive disorder, migraines, obesity, and movement disorders, such as Parkinson's disease, spasticity, and epilepsy. A catheter may also be positioned to deliver insulin to a patient with diabetes. In other examples, the system may deliver a therapeutic fluid to various sites within a patient to facilitate other therapies and to manage other conditions including peripheral neuropathy or post-operative pain mitigation, ilioinguinal nerve therapy, intercostal nerve therapy, gastric drug induced stimulation for the treatment of gastric motility disorders and/or obesity, and muscle stimulation, or for mitigation of peripheral and localized pain e.g., leg pain or back pain.

The techniques described in this disclosure may be implemented, at least in part, in hardware, software, firmware or any combination thereof For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in a computer-readable medium, such as a computer-readable storage medium, containing instructions. Instructions embedded or encoded in a computer-readable storage medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

Various examples have been described. These and other examples are within the scope of the following claims.

The invention claimed is:

1. A therapeutic fluid delivery system comprising:
a reservoir configured to house a therapeutic fluid;
a pressure sensor configured to measure a pressure of the reservoir; and
a processor configured to determine at least one of a difference between an actual rate at which the therapeutic fluid is delivered from the reservoir and a rate at which the therapeutic fluid is expected to be delivered from the reservoir or a difference between an actual volume and an expected volume of therapeutic fluid in the reservoir based on changes in the pressure of the reservoir measured by the pressure sensor over time and detect an unexpected change in a volume of the therapeutic fluid in the reservoir when at least one of the difference between the actual rate at which the therapeutic fluid is delivered from the reservoir and the rate at which the therapeutic fluid is expected to be delivered from the reservoir is greater than a first threshold or the difference between the actual volume and the expected volume of therapeutic fluid in the reservoir is greater than a second threshold,
wherein the first and second thresholds decrease as a time period over which the changes in the pressure of the reservoir are measured by the pressure sensor increases.

2. The system of claim 1, wherein the processor is configured to determine the actual rate at which the therapeutic fluid is delivered from the reservoir at least by dividing a change in the pressure of the reservoir measured by the pressure sensor over a time period by a constant representing the sensitivity of the pressure of the reservoir to changes in the volume of therapeutic fluid in the reservoir.

3. The system of claim 2, wherein the processor is configured to perform a linear regression of the change in the pressure measured by the pressure sensor to normalize the change in the pressure of the reservoir measured by the pressure sensor over the time period for temperature changes in the reservoir.

4. The system of claim 3, wherein the linear regression comprises a least squares linear regression.

5. The system of claim 2, further comprising a temperature sensor configured to measure a temperature of the reservoir, wherein the processor is configured to normalize the change in the pressure of the reservoir measured by the pressure sensor over the time period for temperature changes based on changes in the temperature of the reservoir measured by the temperature sensor over the time period.

6. The system of claim 1, wherein the expected rate at which the therapeutic fluid is delivered from the reservoir corresponds to a rate at which the processor is programmed to control a pump to deliver the therapeutic fluid from the reservoir.

7. The system of claim 6, further comprising a memory configured to store the rate at which the processor is programmed to control the pump to deliver the therapeutic fluid from the reservoir.

8. The system of claim 1, wherein the processor is configured to generate an alert when the difference between the actual rate and the expected rate is greater than the first threshold.

9. The system of claim 1, wherein the processor is configured to determine the actual volume of therapeutic fluid in the reservoir at least by:
   determining the actual rate at which the therapeutic fluid is delivered from the reservoir based on the changes in the pressure of the reservoir measured by the pressure sensor over time;
   multiplying the actual rate by a time period over which the changes in the pressure of the reservoir are measured by the pressure sensor to determine an actual volume of therapeutic fluid delivered from the reservoir over the time period; and
   subtracting the actual volume of therapeutic fluid delivered from the reservoir over the time period from a starting volume of therapeutic fluid in the reservoir.

10. The system of claim 9, wherein the processor is configured to determine the actual rate at which the therapeutic fluid is delivered from the reservoir at least by dividing a change in the pressure of the reservoir measured by the pressure sensor over a time period by a constant representing the sensitivity of the pressure of the reservoir to changes in the volume of therapeutic fluid in the reservoir.

11. The system of claim 9, wherein the processor is configured to perform a linear regression of the change in the pressure measured by the pressure sensor to normalize the change in the pressure of the reservoir measured by the pressure sensor over the time period for temperature changes in the reservoir.

12. The system of claim 1, wherein the processor is configured to determine the expected volume of therapeutic fluid in the reservoir at least by subtracting a volume of therapeutic fluid expected to be delivered from the reservoir over a time period over which the changes in the pressure of the reservoir are measured by the pressure sensor from a starting volume of therapeutic fluid in the reservoir.

13. The system of claim 12, wherein the processor is configured to determine the expected volume of therapeutic fluid delivered from the reservoir at least by multiplying a rate at which the therapeutic fluid is expected to be delivered from the reservoir over the time period by the time period.

14. The system of claim 12, wherein the processor is configured to determine the expected volume of therapeutic fluid delivered from the reservoir at least by multiplying a number of strokes of a pump configured to deliver the therapeutic fluid from the reservoir by a volume of fluid pumped per stroke.

15. The system of claim 1, wherein the processor is configured to generate an alert when the difference between the actual volume and the expected volume is greater than the second threshold.

16. The system of claim 1, wherein the processor is configured to generate an alert when the unexpected change in the volume of therapeutic fluid in the reservoir is detected.

17. The system of claim 16, wherein the alert comprises at least one of an audible, visual, or tactile alert.

18. The system of claim 1 further comprising a fluid delivery device comprising the reservoir, and wherein the processor is configured to cause the fluid delivery device to at least one of vibrate or issue an audible sound when the unexpected change in the volume of therapeutic fluid in the reservoir is detected.

19. The system of claim 18, wherein the fluid delivery device comprises the processor.

20. The system of claim 1 further comprising a programmer, wherein the processor is configured to cause the programmer to at least one of vibrate, issue an audible sound, or display a visual message when the unexpected change in the volume of therapeutic fluid in the reservoir is detected.

21. The system of claim 20, wherein the programmer comprises the processor.

22. The system of claim 1 further comprising a memory configured to store one or more pressures of the reservoir measured by the pressure sensor.

23. The system of claim 1, wherein the first threshold comprises a percentage deviation between the actual rate at which the therapeutic fluid is delivered from the reservoir and the rate at which the therapeutic fluid is expected to be delivered from the reservoir.

24. The system of claim 23, wherein the time period over which the changes in the pressure of the reservoir are measured by the pressure sensor is less than or equal to 24 hours and wherein the first threshold comprises a percentage deviation between the actual and expected fluid delivery rates approximately equal to +/−500% such that the processor detects the unexpected change in the volume of therapeutic fluid in the reservoir when the actual rate at which the therapeutic fluid is delivered from the reservoir deviates from the rate at which the therapeutic fluid is expected to be delivered from the reservoir by greater than or equal to +/−500%.

25. The system of claim 23, wherein the time period over which the changes in the pressure of the reservoir are measured by the pressure sensor is greater than 24 hours and less than 120 hours and wherein the first threshold comprises a percentage deviation between the actual and expected fluid delivery rates approximately equal to +/−100% such that the processor detects the unexpected change in the volume of therapeutic fluid in the reservoir when the actual rate at which the therapeutic fluid is delivered from the reservoir deviates from the rate at which the therapeutic fluid is expected to be delivered from the reservoir by greater than or equal to +/−100%.

26. The system of claim 23, wherein the time period over which the changes in the pressure of the reservoir are measured by the pressure sensor is greater than 120 hours and less than 168 hours and wherein the first threshold comprises a percentage deviation between the actual and expected fluid delivery rates approximately equal to +/−25% such that the processor detects the unexpected change in the volume of therapeutic fluid in the reservoir when the actual rate at which the therapeutic fluid is delivered from the reservoir deviates from the rate at which the therapeutic fluid is expected to be delivered from the reservoir by greater than or equal to +/−25%.

27. The system of claim 23, wherein the time period over which the changes in the pressure of the reservoir are measured by the pressure sensor is greater than 168 hours and wherein the first threshold comprises a percentage deviation between the actual and expected fluid delivery rates approximately equal to +/−12% such that the processor detects the unexpected change in the volume of therapeutic fluid in the reservoir when the actual rate at which the therapeutic fluid is delivered from the reservoir deviates from the rate at which the therapeutic fluid is expected to be delivered from the reservoir by greater than or equal to +/−12%.

28. A method comprising:
measuring a pressure of a reservoir of a fluid delivery device with a pressure sensor;
determining at least one of a difference between an actual rate at which the therapeutic fluid is delivered from the reservoir and a rate at which the therapeutic fluid is expected to be delivered from the reservoir or a difference between an actual volume and an expected volume of therapeutic fluid in the reservoir based on changes in the pressure of the reservoir measured by the pressure sensor over time; and
detecting an unexpected change in a volume of therapeutic fluid in the reservoir when at least one of the difference between the actual rate at which the therapeutic fluid is delivered from the reservoir and the rate at which the therapeutic fluid is expected to be delivered from the reservoir is greater than a first threshold or the difference between the actual volume and the expected volume of therapeutic fluid in the reservoir is greater than a second threshold,
wherein the first and second thresholds decrease as a time period over which the changes in the pressure of the reservoir are measured by the pressure sensor increases.

29. The method of claim 28, wherein determining the actual rate at which the therapeutic fluid is delivered from the reservoir comprises dividing a change in the pressure of the reservoir measured by the pressure sensor over a time period by a constant representing the sensitivity of the pressure of the reservoir to changes in the volume of therapeutic fluid in the reservoir.

30. The method of claim 29 further comprising performing a linear regression of the change in the pressure measured by the pressure sensor to normalize the change in the pressure of the reservoir measured by the pressure sensor over the time period for temperature changes in the reservoir.

31. The method of claim 30, wherein the linear regression comprises a least squares linear regression.

32. The method of claim 29 further comprising normalizing the change in the pressure of the reservoir measured by the pressure sensor over the time period for temperature changes in the reservoir based on changes in the temperature of the reservoir measured by a temperature sensor over the time period.

33. The method of claim 28 further comprising generating an alert when the difference between the actual rate and the expected rate is greater than the first threshold.

34. The method of claim 33, wherein the alert comprises at least one of an audible, visual, or tactile alert.

35. The method of claim 28 further comprising causing the fluid delivery device to at least one of vibrate or issue an audible sound when the unexpected change in the volume of therapeutic fluid in the reservoir is detected.

36. A non-transitory computer-readable storage medium comprising instructions for causing a programmable processor to:
cause a pressure sensor to measure a pressure of a reservoir of a fluid delivery device with a pressure sensor;
determine at least one of a difference between an actual rate at which the therapeutic fluid is delivered from the reservoir and a rate at which the therapeutic fluid is expected to be delivered from the reservoir or a difference between an actual volume and an expected volume of therapeutic fluid in the reservoir based on changes in the pressure of the reservoir measured by the pressure sensor over time; and
detect an unexpected change in a volume of therapeutic fluid in the reservoir when at least one of the difference between the actual rate at which the therapeutic fluid is delivered from the reservoir and the rate at which the therapeutic fluid is expected to be delivered from the reservoir is greater than a first threshold or the difference between the actual volume and the expected volume of therapeutic fluid in the reservoir is greater than a second threshold,
wherein the first and second thresholds decrease as a time period over which the changes in the pressure of the reservoir are measured by the pressure sensor increases.

37. A fluid delivery system comprising:
means for measuring a pressure of a reservoir of a fluid delivery device;
means for determining at least one of a difference between an actual rate at which the therapeutic fluid is delivered from the reservoir and a rate at which the therapeutic fluid is expected to be delivered from the reservoir or a difference between an actual volume and an expected volume of therapeutic fluid in the reservoir based on changes in the pressure of the reservoir measured over time by the means for measuring the pressure of the reservoir; and
means for detecting an unexpected change in a volume of therapeutic fluid in the reservoir when at least one of the difference between the actual rate at which the therapeutic fluid is delivered from the reservoir and the rate at which the therapeutic fluid is expected to be delivered from the reservoir is greater than a first threshold or the difference between the actual volume and the expected volume of therapeutic fluid in the reservoir is greater than a second threshold,
wherein the first and second thresholds decrease as a time period over which the changes in the pressure of the reservoir are measured by the means for measuring the pressure of the reservoir increases.

38. A therapeutic fluid delivery system comprising:
an outer housing;
a reservoir within the outer housing and configured to house a therapeutic fluid;
a pressure sensor configured to measure a first pressure of the therapeutic fluid in the reservoir at a first time and a second pressure of the therapeutic fluid in the reservoir at a second time;
an ambulatory reservoir fluid volume gauge; and a processor configured to receive the first pressure of the therapeutic fluid in the reservoir and the second pressure of the therapeutic fluid in the reservoir, determine a change in pressure of the therapeutic fluid in the reservoir over time between the first pressure and the second pressure measured by the pressure sensor, determine an actual volume of the therapeutic fluid in the reservoir based on the change in pressure of the therapeutic fluid in the reservoir determined by the processor, and control the ambulatory fluid volume gauge to indicate the actual volume of the therapeutic fluid in the reservoir, wherein the ambulatory reservoir fluid volume gauge comprises a visual representation of the actual volume of the therapeutic fluid in the reservoir.

39. The system of claim 38, wherein the ambulatory reservoir fluid volume gauge comprises a display of the visual representation of the actual volume of the therapeutic fluid in the reservoir.

40. The system of claim 39, wherein the ambulatory reservoir fluid volume gauge comprises at least one of a text or graphical representation of the actual volume of the therapeutic fluid in the reservoir.

41. The system of claim 39 further comprising a programmer, wherein the programmer comprises the ambulatory reservoir fluid volume gauge.

42. The system of claim 38, wherein the processor is configured to determine the actual volume of therapeutic fluid in the reservoir at least by:
determining an actual rate at which the therapeutic fluid is delivered from the reservoir based on the change in pressure of the therapeutic fluid in the reservoir measured by the pressure sensor; and
determining the actual volume of the therapeutic fluid in the reservoir based on the actual rate at which the therapeutic fluid is delivered from the reservoir.

43. The system of claim 42, wherein the processor is configured to determine the actual rate at which the therapeutic fluid is delivered from the reservoir at least by dividing the change in pressure of the therapeutic fluid in the reservoir measured by the pressure sensor over a time period by a constant representing the sensitivity of the pressure of the reservoir to changes in the volume of the therapeutic fluid in the reservoir.

44. The system of claim 43, wherein the processor is configured to normalize the change in pressure of the therapeutic fluid in the reservoir measured by the pressure sensor over the time period for temperature changes at least by performing a linear regression of the change in the pressure measured by the pressure sensor.

45. The system of claim 44, wherein the linear regression comprises a least squares linear regression.

46. The system of claim 43 further comprising a temperature sensor configured to measure a temperature of the reservoir, wherein the processor is configured to normalize the change in pressure of the therapeutic fluid in the reservoir measured by the pressure sensor over the time period for temperature changes based on changes in the temperature of the reservoir measured by the temperature sensor over the time period.

47. The system of claim 38, wherein the processor is configured to determine the actual volume of the therapeutic fluid in the reservoir at least by integrating the actual rate at which the therapeutic fluid is delivered from the reservoir over a time period over which the change in pressure of the therapeutic fluid in the reservoir are measured by the pressure sensor.

48. A method comprising:
measuring a first pressure of a therapeutic fluid in a reservoir of a fluid delivery device at a first time and a second pressure of the therapeutic fluid in the reservoir at a second time with a pressure sensor;
receiving the first pressure of the therapeutic fluid in the reservoir and the second pressure of the therapeutic fluid in the reservoir;
determining a change in pressure of the therapeutic fluid in the reservoir over time between the first pressure and the second pressure measured by the pressure sensor;
determining an actual volume of therapeutic fluid in the reservoir based on the change in pressure of the therapeutic fluid in the reservoir determined by the processor; and
controlling an ambulatory fluid volume gauge to indicate the actual volume of the therapeutic fluid in the reservoir,
wherein the ambulatory reservoir fluid volume gauge comprises a visual representation of the actual volume of the therapeutic fluid in the reservoir.

49. The method of claim 48, wherein the ambulatory reservoir fluid volume gauge comprises a display of the visual representation of the actual volume the of therapeutic fluid in the reservoir.

50. The method of claim 49, wherein the ambulatory reservoir fluid volume gauge comprises at least one of a text or graphical representation of the actual volume of the therapeutic fluid in the reservoir.

51. The method of claim 48, wherein determining the actual volume of the therapeutic fluid in the reservoir comprises:
determining an actual rate at which the therapeutic fluid is delivered from the reservoir based on the change in pressure of the therapeutic fluid in the reservoir measured by the pressure sensor; and
determining the actual volume of the therapeutic fluid in the reservoir based on the actual rate at which the therapeutic fluid is delivered from the reservoir.

52. The method of claim 51, wherein determining the actual rate at which the therapeutic fluid is delivered from the reservoir comprises dividing the change in pressure of the reservoir measured by the pressure sensor over a time period by a constant representing the sensitivity of the pressure of the therapeutic fluid in the reservoir to changes in the volume of the therapeutic fluid in the reservoir.

53. The method of claim 51, further comprising normalizing the change in pressure of the therapeutic fluid in the reservoir measured by the pressure sensor over the time period for temperature changes at least by performing a linear regression of the change in the pressure measured by the pressure sensor.

54. The method of claim 53, wherein the linear regression comprises a least squares linear regression.

55. The method of claim 48, wherein determining the actual volume of the therapeutic fluid in the reservoir comprises integrating the actual rate at which the therapeutic fluid is delivered from the reservoir over a time period over which the change in pressure of the therapeutic fluid in the reservoir are measured by the pressure sensor.

56. A fluid delivery system comprising:
means for measuring a first pressure of a therapeutic fluid in a reservoir of a fluid delivery device at a first time and a second pressure of the therapeutic fluid in the reservoir at a second time;

means for receiving the first pressure of the therapeutic fluid in the reservoir and the second pressure of the therapeutic fluid in the reservoir;

means for determining a change in pressure of the therapeutic fluid in the reservoir over time between the first pressure and the second pressure measured by the pressure sensor;

means for determining an actual volume of therapeutic fluid in the reservoir based on the change in pressure of the therapeutic fluid in the reservoir determined by the means for determining the change in pressure of the therapeutic fluid in the reservoir over time; and means for controlling an ambulatory fluid volume gauge to indicate the actual volume of the therapeutic fluid in the reservoir, wherein the ambulatory reservoir fluid volume gauge comprises a visual representation of the actual volume of the therapeutic fluid in the reservoir.

57. A non-transitory computer-readable storage medium comprising instructions for causing a programmable processor to:

measure a first pressure of a therapeutic fluid in a reservoir of a fluid delivery device at a first time and a second pressure of the therapeutic fluid in the reservoir at a second time with a pressure sensor;

receive the first pressure of the therapeutic fluid in the reservoir and the second pressure of the therapeutic fluid in the reservoir;

determine a change in pressure of the therapeutic fluid in the reservoir over time between the first pressure and the second pressure measured by the pressure sensor;

determine an actual volume of therapeutic fluid in the reservoir based on the change in pressure of the therapeutic fluid in the reservoir determined by the programmable processor; and control an ambulatory fluid volume gauge to indicate the actual volume of the therapeutic fluid in the reservoir, wherein the ambulatory reservoir fluid volume gauge comprises a visual representation of the actual volume of the therapeutic fluid in the reservoir.

58. A method comprising:

measuring a pressure of a therapeutic fluid in a reservoir of a fluid delivery device with a pressure sensor;

determining an actual rate at which the therapeutic fluid is delivered from the reservoir based on changes in the pressure of the therapeutic fluid in the reservoir measured by the pressure sensor;

integrating the actual rate at which the therapeutic fluid is delivered from the reservoir over a period of time over which changes in the pressure of the therapeutic fluid in the reservoir are measured by the pressure sensor to determine an actual volume of therapeutic fluid in the reservoir; and controlling an ambulatory fluid volume gauge to indicate the actual volume of the therapeutic fluid in the reservoir, wherein the ambulatory reservoir fluid volume gauge comprises a visual representation of the actual volume of the therapeutic fluid in the reservoir.

59. The method of claim 58, wherein determining the actual rate at which the therapeutic fluid is delivered from the reservoir comprises dividing a change in the pressure of the therapeutic fluid in the reservoir measured by the pressure sensor over a time period by a constant representing the sensitivity of the pressure of the reservoir to changes in the volume of the therapeutic fluid in the reservoir.

60. The method of claim 59 further comprising normalizing the change in the pressure of the therapeutic fluid in the reservoir measured by the pressure sensor over the time period for temperature changes at least by performing a linear regression of the change in the pressure measured by the pressure sensor.

* * * * *